United States Patent
Dubowchik et al.

(12) 
(10) Patent No.: US 6,228,872 B1
(45) Date of Patent: May 8, 2001

(54) NEUROTROPHIC DIAMIDE AND CARBAMATE AGENTS

(75) Inventors: Gene M. Dubowchik, Middlefield; Jonathan L. Ditta; David P. Provencal, both of Middletown; Derek J. Denhart, Wallingford, all of CT (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 09/435,529

(22) Filed: Nov. 8, 1999

Related U.S. Application Data

(60) Provisional application No. 60/108,060, filed on Nov. 12, 1998.

(51) Int. Cl.$^7$ .......................... A61K 31/445; A61K 31/40; C07D 211/18; C07D 211/30

(52) U.S. Cl. .......................... 514/343; 514/343; 514/414; 514/423; 546/279.1; 548/467; 548/530

(58) Field of Search .................................... 514/343, 414, 514/423; 546/279.1; 548/467, 530

(56) References Cited

U.S. PATENT DOCUMENTS

| | | | |
|---|---|---|---|
| 5,192,773 | 3/1993 | Armistead et al. | 514/315 |
| 5,330,993 | 7/1994 | Armistead et al. | 514/330 |
| 5,516,797 | 5/1996 | Armistead et al. | 514/548 |
| 5,622,970 | 4/1997 | Armistead et al. | 514/315 |
| 5,654,332 * | 8/1997 | Armistead | 514/533 |
| 5,696,135 | 12/1997 | Steiner et al. | 514/317 |
| 5,721,256 | 2/1998 | Hamilton et al. | 514/330 |
| 5,780,484 | 7/1998 | Zelle et al. | 514/316 |
| 5,786,378 | 7/1998 | Hamilton et al. | 514/423 |
| 5,795,908 | 8/1998 | Hamilton et al. | 514/423 |
| 5,798,355 | 8/1998 | Steiner et al. | 514/248 |
| 5,801,187 | 9/1998 | Li et al. | 514/365 |
| 5,801,197 | 9/1998 | Steiner et al. | 514/548 |

FOREIGN PATENT DOCUMENTS

| | | |
|---|---|---|
| 0405994 | 1/1991 | (EP) . |
| 0564924 | 10/1993 | (EP) . |
| WO92/19593 | 11/1992 | (WO) . |
| WO92/21313 | 12/1992 | (WO) . |
| WO94/07858 | 4/1994 | (WO) . |
| WO96/40140 | 12/1996 | (WO) . |
| WO96/40633 | 12/1996 | (WO) . |
| WO96/41609 | 12/1996 | (WO) . |
| WO97/16190 | 5/1997 | (WO) . |
| WO97/36869 | 10/1997 | (WO) . |
| WO98/13343 | 4/1998 | (WO) . |
| WO98/13355 | 4/1998 | (WO) . |
| WO98/20891 | 5/1998 | (WO) . |
| WO98/20892 | 5/1998 | (WO) . |
| WO98/20893 | 5/1998 | (WO) . |
| WO98/29116 | 7/1998 | (WO) . |
| WO98/29117 | 7/1998 | (WO) . |

OTHER PUBLICATIONS

A. Ruhlmann, et al, "Effects of the Immunosuppressive Drugs CsA and FK 506 on Intracellular Signalling and Gene Regulation," Immunobiol., 198, pp. 192–206, 1997.

S.L. Schreiber, et al, "Molecular Recognition of Immunophilins and Immunophilin–Ligand Complexes," Tetrahedron, 48(13), pp. 2545–2558, 1992.

T. Wang, et al, "Specific Interaction of Type I Receptors of the TGF–β Family with the Immunophilin FKBP–12," Science, 265, pp. 674–676, 1994.

A.M. Cameron, et al, "FKBP12 Binds the Inositol 1,4, 5–Trisphosphate Receptor at Leucine–Proline (1400–1401) and Anchors Calcineurin to this FK506–Like Domain," J. Biol. Chem., 272(44), pp. 27582–27588, 1997.

T. Wang, et al, "The Immunophilin FKPB12 Functions as a Common Inhibitor of the TGFβ Family Type I Receptors," Cell, 86, pp. 435–444, 1996.

D.S. Yamashita, et al, "Design, Synthesis and Evaluation of Dual Domain FKBP Ligands," Bioorg. Med. Chem. Lett., 4(2), pp. 325–328, 1994.

D.M. Armistead, et al, "Design, Synthesis and Structure of Non–Macrocyclic Inhibitors of FKBP12, the Major Binding Protein for the Immunosuppressant FK506," Acta Cryst. D., 51, pp. 522–528, 1995.

W.E. Lyons, et al, "Immunosuppressant FK506 Promotes Neurite Outgrowth in Cultures of PC12 Cells and Sensory Ganglia," Proc. Natl. Acad. Sci. USA, 91, pp. 3191–3195, 1994.

B.G. Gold, et al, "The Immunosuppressant FK506 Increases the Rate of Axonal Regeneration in Rat Sciatic Nerve," J. Neuroscience, 15(11), pp. 7509–7516, 1995.

G.S. Hamilton, et al, "Neuroimmunophilin Ligands as Novel Therapeutics for the Treatment of Degnerative Disorders of the Nervous System," Curr. Pharm. Design, 3, pp. 405–428, 1997.

B.G. Gold, et al, "A Nonimmunosuppressant FKPB–12 Ligand Increases Nerve Regeneration," Exp. Neurology, 147, pp. 269–278, 1997.

S.H. Snyder, et al, "Immunophilins and the Nervous System," Nature Medicine, 1(1), pp. 32–37, 1995.

(List continued on next page.)

*Primary Examiner*—Richard L. Raymond
(74) *Attorney, Agent, or Firm*—Samuel J. DuBoff

(57) ABSTRACT

The present invention relates to the design, synthesis, and the peptidyl-prolyl isomerase (PPIase or rotamase) inhibitory activity of novel pyrrolidinemethyl diamide and carbamate compounds that are neurotrophic agents (i.e. compounds capable of stimulating growth or proliferation of nervous tissue) and that bind to immunophilins such as FKBP12 and inhibit their rotamase activity. This invention also relates to pharmaceutical compositions comprising these compounds.

7 Claims, No Drawings

OTHER PUBLICATIONS

B.G. Gold, et al, "the Immunosuppressant FK506 Increases GAP–43 mRNA Levels in Azotomized Sensory Neurons," Neuroscience Letters, 241, pp. 25–28, 1998.

J.L. Kofron, et al, "Determination of Kinetic Constants for Peptidyl Prolyl Cis–Trans Isomerases by an Improved Spectrophotometric Assay," Biochemistry, 30, pp. 6127–6134, 1991.

U.A. Germann, et al, "Cellular and Biochemical Characterization of VX–710 as a Chemosensitizer: Reversal of P–Glycoprotein–Mediated Multidrug Resistance In Vitro," Anti–Cancer Drugs, 8, pp. 125–140, 1997.

J.R. Hauske, et al, "Investigation of the Effects of Synthetic, Non–Cytotoxic Immunophilin Inhibitors on MDR," Bioorg. Med. Chem. Lett., 4(17), pp. 2097–2102, 1994.

M.M. Endrich, et al, "The V3 Loop of Human Immunodeficiency Virus Type–1 Envelope Protein is a High–Affinity Ligand for Immunophilins Present in Human Blood," Eur. J. Biochem., 252, pp. 441–446, 1998.

A. Karpas, et al, "Inhibition of Human Immunodeficiency Virus and Growth of Infected T Cells by the Immunosuppressive Drugs Cyclosporin A and FK506," Proc. Natl. Acad. Sci. USA, 89, pp. 8351–8355, 1992.

* cited by examiner-

NEUROTROPHIC DIAMIDE AND CARBAMATE AGENTS

CROSS-REFERENCE TO RELATED APPLICATIONS

This application claims the priority of U.S. Provisional Application Serial No. 60/108,060 filed Nov. 12, 1998.

BACKGROUND OF THE INVENTION

Immunophilins are cytosolic proteins that possess peptidyl-prolyl-cis-trans isomerase (PPIase or rotamase) activity. This family of proteins behave as chaperone molecules causing cis-trans isomerization of peptide-prolyl bonds that could be a rate limiting step in the correct folding of certain proteins. They are also involved in many cellular signal transduction pathways as partners in multiprotein complexes for which binding in the rotamase active site, but not rotamase activity per se, appears to be important (R ühlmann, et al., *Immunobiol.*, 198, pp. 192–206 (1998)). Immunosuppressive drugs such as FK506, rapamycin and cyclosporin A bind to specific groups of immunophilins. FK506 and rapamycin bind to the so-called FK506-binding proteins (FKBPs), whereas the cyclophilins binds to cyclosporin A. It has been shown that binding to the 12kD immunophilin FKBP12 is necessary for FK506 to elicit its immunosuppressive activity. Subsequently, it was also found that FK506 has two binding domains: one that binds to FKBP12 and the other (the effector domain) for the complex of FK506 and FKBP12 that binds to the serine/threonine phosphatase, calcineurin. This complexation inhibits calcineurin and prevents the proliferation of T-lymphocytes (i.e. immunosuppression). Rapamycin has an effector domain of a different structure, and its complex with FKBP12 binds to a different target protein that, also results in immunosuppression. For a review, see S. L. Schreiber, et al., *Tetrahedron*, 48, pp. 2545–2558 (1992). Some of the other proteins with which FKBP12 is known to interact include the TGFβ receptor I (Wang, et al., *Science*, 265, pp. 674–676 (1994)), the $IP_3$ receptor and the ryanodine receptor (Cameron, et al., *J. Biol. Chem.*, 272, pp. 27582–27588 (1997)). In the case of the TGFβ system, it has been suggested that FKBP12 binding inhibits unregulated signalling with consequences for differentiation, apoptosis and proliferation (Wang, et al., *Cell*, 86, pp. 435–444 (1996)).

While FK506 exhibits immunosuppressive effects, analogs lacking the calcineurin binding effector domain are devoid of immunosuppressive activity. Many small molecules that contain the essential elements of the FKBP12 binding domain of FK506 but lack the calcineurin binding domain were found to retain high affinity binding to FKBP12, and behave as rotamase inhibitors (D. S. Yamshita, et al., *Bioorg. Med. Chem. Lett.*, 4, pp. 325–328 (1994); D. M. Armistead, et al., *Acta Cryst. D*, 51, pp. 522–528 (1995)).

FK506 has been shown to possess neurotrophic properties in vitro and in vivo (W. E. Lyons, et al., *Proc. Natl. Acad. Sci USA*, 91, pp. 3191–3195 (1994); B. G. Gold, et al., *J. Neurosci.*, 15, pp. 7509–7516 (1995)). However, its immunosuppressive properties as well as other serious side effects are drawbacks to its use as a neuroregenerative agent. Recently, in vitro studies in PC12 cells, SY5Y cells, and chick sensory dorsal root ganglion explant cultures have shown that small molecule, nonimmunosuppressive FKBP12 rotamase inhibitors also promote neurite outgrowth, and a number of these compounds have shown utility in reversal of CNS lesioning and nerve crush in animal models (G. S. Hamilton, et al., *Curr. Pharm. Design*, 3, pp. 405–428 (1997); B. G. Gold, et al., *Exp. Neurol.*, 147, pp. 269–278 (1997)). Thus, while the calceineurin binding domain of FK506 is necessary for immunosuppressive activity, it is not required for neurotrophic activity.

A 10–50 fold elevated expression of immunophilins in the central nervous system in comparison with the immune system is well documented (S. H. Snyder, et al., *Nature Med.*, 1, pp. 32–37 (1995)). Recently, augmented expression of FKBP12 m-RNA following facial nerve crush and sciatic nerve lesions was established in facial and lumbar motor neurons. The observed augmentation paralleled the enhanced expression of growth associated protein GAP43 mRNA (B. G. Gold, et al., *Neurosci. Lett.*, 241, pp. 25–28 (1998)). These observations make FKBP12 an attractive target for developing nonimmunosuppressive rotamase inhibitors which promote neurite outgrowth. Such compounds are potential therapeutics to reverse neuronal damage caused by neurodegenerative disease or physical trauma.

There have been disclosures of related compounds for overcoming multidrug resistance (MDR) or as immunosuppressants such as:

WO 94/07858 published Apr. 14, 1994
WO 92/19593 published Nov. 12, 1992
U.S. Pat. No. 5,622,970 granted Apr. 22, 1997
U.S. Pat. No. 5,330,993 granted Jul. 19, 1994
U.S. Pat. No. 5,192,773 granted Mar. 9, 1993
U.S. Pat. No. 5,516,797 granted May 14, 1996
WO 92/21313 published Dec. 10, 1992
European Application 564924 published Oct. 13, 1993
European Application 405994 published Jan. 2, 1991

Other prior art disclosing related compounds having neurotrophic activity are:

WO 96/40140 published Dec. 19, 1996
WO 96/40633 published Dec. 19, 1996
WO 97/16190 published May 9, 1997
WO 96141609 published Dec. 27, 1996
U.S. Pat. No. 5,696,135 granted Dec. 9, 1997
WO 97/36869 published Oct. 9, 1997
U.S. Pat. No. 5,721,256 granted Feb. 24, 1998
U.S. Pat. No. 5,654,332 granted Aug. 5, 1997
WO 98/13343 published Apr. 2, 1998
WO 98/13355 published Apr. 2, 1998
WO 98/20891 published May 22, 1998
WO 98/20892 published May 22, 1998
WO 98/20893 published May 22, 1998
WO 98/29116 published Jul. 9, 1998
WO 98/29117 published Jul. 9, 1998
U.S. Pat. No. 5,780,484 granted Jul. 14, 1998
U.S. Pat. No. 5,786,378 granted Jul. 28, 1998
U.S. Pat. No. 5,795,908 granted Aug. 18, 1998
U.S. Pat. No. 5,798,355 granted Aug. 25, 1998
U.S. Pat. No. 5,801,187 granted Sep. 1, 1998
U.S. Pat. No. 5,801,197 granted Sep. 1, 1998

Since there are relatively few EKBP12-binding compounds that are known to stimulate neurite growth, there remains a great need for additional neurotrophic, FKBP12-binding compounds.

SUMMARY OF THE INVENTION

Surprisingly, applicant has solved the aforementioned problem. The present invention relates to novel diamide and carbamate compounds and pharmaceutical compositions thereof that possess neurotrophic properties.

DETAILED DESCRIPTION OF THE INVENTION

According to one embodiment, the present invention provides:

A compound with affinity for an FK506 binding protein having the formula (I):

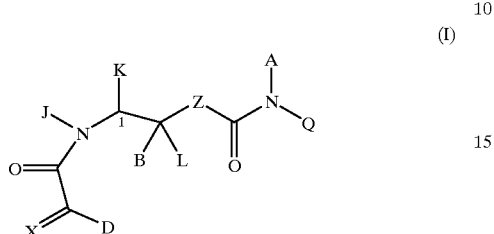

(I)

and pharmaceutically acceptable salts thereof, wherein:

Z is O, NH, N($C_1$–$C_3$)-alkyl or $CH_2$;

X is O or $F_2$;

B and L are independently hydrogen, ($C_1$–$C_4$)-alkyl, or benzyl;

J is hydrogen, ($C_1$–$C_4$)-alkyl or benzyl;

K is ($C_1$–$C_4$)-straight or branched alkyl, benzyl or cyclohexylmethyl, or wherein J and K may be taken together to form a 4–7 membered heterocyclic ring which may contain a heteroatom selected from the group consisting of O, S, SO or $SO_2$, N, and NR, wherein R is selected from the group consisting of hydrogen, ($C_1$–$C_4$)-straight or branched alkyl, ($C_2$–$C_4$)-straight or branched alkenyl or alkynyl, and ($C_1$–$C_4$)-bridging alkyl wherein a bridge is formed between the nitrogen and a carbon atom of said heteroatom-containing chain to form a ring, and wherein said ring is optionally fused to an Ar group; wherein the stereochemistry at carbon position 1 is R or S; D is ($C_1$–$C_6$)-straight or branched alkyl, ($C_2$–$C_6$) straight or branched alkenyl, ($C_5$–$C_7$)-cycloalkyl or ($C_5$–$C_7$)ycloalkenyl substituted with ($C_1$–$C_4$)- straight or branched alkyl or ($C_2$–$C_4$)-straight or branched alkenyl, O-($C_1$–$C_4$)-straight or branched alkyl, O-($C_2$–$C_4$)-straight or branched alkenyl, 2-indolyl, 3-indolyl, [($C_1$–$C_4$)-alkyl or ($C_2$–$C_4$)- alkenyl]-Ar or Ar;

Ar is a carbocyclic aromatic group selected from the group consisiting of phenyl, 1-naphthyl, 2-naphthyl, indenyl, azulenyl, fluorenyl, and anthracenyl; or a heterocyclic aromatic group selected from the group consisting of 2-furyl, 3-furyl, 2-thienyl, 3-thienyl, 2-pyridyl, 3-pyridyl, 4-pyridyl, pyrrolyl, oxazolyl, thiazolyl, imidazolyl, pyrazolyl, isoxazolyl, isothiazolyl, 1,2,3-oxadiazolyl, 1,2,3-triazolyl, 1,3, 4-thiadiazolyl, pyridazinyl, pyrimidinyl, pyrazinyl, 1,3,5-triazinyl, 1,3,5-trithianyl, indolizinyl, indolyl, isoindolyl, 3H-indolyl, indolinyl, benzo[b]furanyl, benzo[b]thiophenyl, 1H-indazolyl, benzimidazolyl, benzthiazolyl, purinyl, 4H-quinolizinyl, quinolinyl, isoquinolinyl, cinnolinyl, phthalazinyl, quinazolinyl, quinoxalinyl, 1,8-naphthyridinyl, pteridinyl, carbazolyl, acridinyl, phenazinyl, phenothiazinyl, and phenoxazinyl;

Ar may contain one to three substituents which are independently selected from the group consisting of hydrogen, halogen, hydroxyl, hydroxymethyl, nitro, trifluoromethyl, trifluoromethoxy, ($C_1$–$C_6$)-straight or branched alkyl, ($C_2$–$C_6$)-straight or branched alkenyl, O-[($C_1$–$C_4$)-straight or branched alkyl], O-benzyl, O-phenyl, 1,2-methylenedioxy, amino, carboxyl, N-[($C_1$–$C_5$)-straight or branched alkyl or ($C_2$–$C_5$)-straight or branched alkenyl] carboxamides, N,N-di-[($C_1$–$C_5$)-straight or branched alkyl or ($C_2$–$C_5$)-straight or branched alkenyl] carboxamides, N-morpholinecarboxamide, N-benzylcarboxamide, N-thiomorpholinocarboxamide, N-picolinoylcarboxamide, O—W, $CH_2$—$(CH_2)_p$— W, O—$(CH_2)_p$—W, $(CH_2)_p$—O—W, and CH=CH—W;

W is 4-methoxyphenyl, 2-pyridyl, 3-pyridyl, 4-pyridyl, pyrazyl, quinolyl, 3,5-dimethylisoxazoyl, isoxazoyl, 2-methylthiazoyl, thiazoyl, 2-thienyl, 3-thienyl, or pyrimidyl; p is 0–2;

Q and A are independently hydrogen, Ar, ($C_1$–$C_{10}$)- straight or branched alkyl, ($C_2$–$C_{10}$)-straight or branched alkenyl or alkynyl, provided the carbon atom having the triple bond in the alkynyl group is not directly bonded to the nitrogen atom of the core; ($C_5$–$C_7$)cycloalkyl substituted ($C_1$–$C_6$)-straight or branched alkyl, ($C_2$–$C_6$)-straight or branched alkenyl or alkynyl, ($C_5$–$C_7$)-cycloalkenyl substituted ($C_1$–$C_6$)-straight or branched alkyl, ($C_2$–$C_6$)-straight or branched alkenyl or alkynyl, or Ar-substituted ($C_1$–$C_6$)-straight or branched alkyl, ($C_2$–$C_6$)-straight or branched alkenyl or alkynyl wherein, in each case, any one of the $CH_2$ groups of said alkyl, alkenyl or alkynyl chains may be optionally replaced by a heteroatom selected from the group consisting of O, S, SO, $SO_2$, N, and NR, wherein R is selected from the group consisting of hydrogen, ($C_1$–$C_4$)-straight or branched alkyl, ($C_2$–$C_4$)-straight or branched alkenyl or alkynyl, and ($C_1$–$C_4$)-bridging alkyl wherein a bridge is formed between the nitrogen and a carbon atom of said heteroatom-containing chain to form a ring, and wherein said ring is optionally fused to an Ar group; or

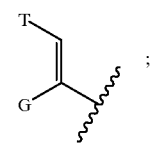

G is hydrogen, ($C_1$–$C_6$)-straight or branched alkyl or ($C_2$–$C_6$)-straight or branched alkenyl or alkynyl; and T is Ar or substituted 5–7 membered cycloalkyl with substituents at positions 3 and 4 which are independently selected from the group consisting of oxo, hydrogen, hydroxyl, O-($C_1$–$C_4$)-alkyl, or O-($C_2$–$C_4$)-alkenyl.

A preferred embodiment are compounds of formula I wherein

J and K are taken together to form a pyrrolidine ring;

the stereochemistry at carbon 1 is S;

B and L are each hydrogen;

X is $F_2$ or O;

Z is O or $CH_2$;

D is 3, 4, 5-trimethoxyphenyl or t-butyl;

A is 3-(3-pyridyl)propyl or 4-(3-pyridyl)butyl; and

Q is phenyl-substituted ($C_1$–$C_6$)-straight or branched chain alkyl, wherein phenyl is optionally substituted with one to teeee substituants independently selected from (C₁–C₆) alkyl, O-(C₁–C₆) alkyl, carboxyl and trifluoromethyl, wherein said alkyl is straight or branched.

Another preferred embodiment are compounds of formula I wherein

Q is 3-phenylpropyl;

3-(3,4,5-trimethoxyphenyl)propyl;

2-(3,4-dimethoxyphenyl)ethyl;

2-phenylethyl;

4-phenylbutyl;

4-(3,4-dimethoxyphenyl)butyl;

3-(4-carboxyphenyl)propyl;

2-(3-methoxyphenyl)ethyl;

2-(3-trifluoromethylphenyl)ethyl, or 3-(4-methoxypbenyl)propyl.

Another aspect of the present invention provides for a pharmaceutical composition which comprises as an active ingredient an amount of a compound of formula I, or a pharmaceutically acceptable salt thereof, effective for stimulating neurite growth in nerve cells, and one or more pharmaceutically acceptable carriers, excipients or diluents thereof.

Another aspect of the present invention provides for a method for stimulating neurite growth in nerve cells comprising the step of contacting said nerve cells with a composition comprising a neurotrophic amount of a compound of formula I with affinity for an FK-506 binding protein.

Another aspect of the present invention provides for a method for stimulating neurite growth in nerve cells comprising the step of contacting said nerve cells with a composition comprising a neurotrophic amount of a compound of formula I with affinity for FKBP12.

GENERAL SUMMARY OF COMPOUND PREPARATION

The carbamates of this invention are best prepared according to the general scheme shown below. Aminoalcohol nitrogens are protected by acylation with di-t-butyl carbonate and the resulting carbamate alcohols are treated with p-nitrophenyl chloroformate to give activated carbonates. These can be coupled with amines, in the presence of catalytic hydroxybenzotriazole, to give Boc-protected carbamates. The Boc protecting group is removed by exposure to hydrogen chloride, and the resulting amine is acylated to give the target compounds.

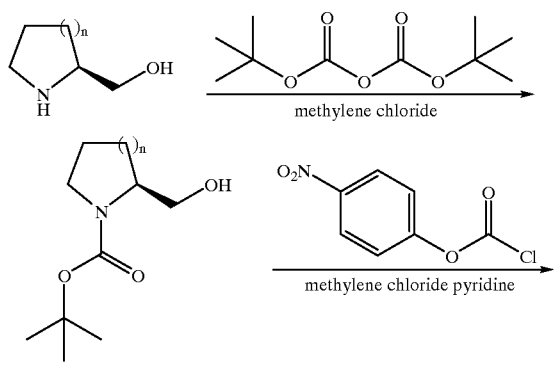

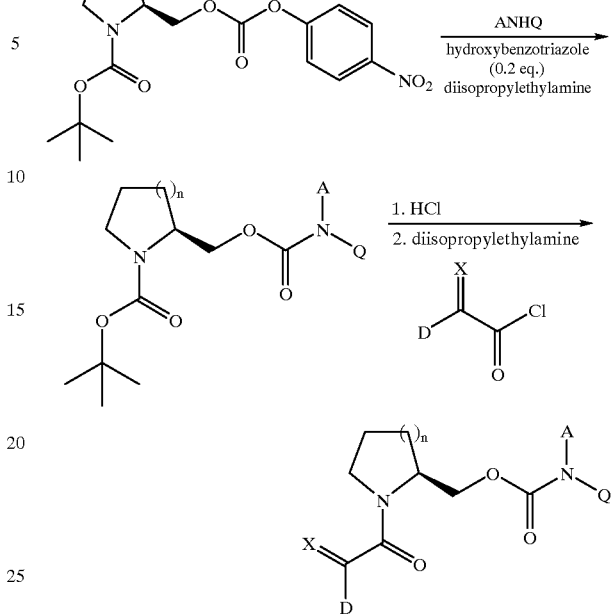

Alternatively, the carbamates of the present invention can also be prepared according to the general scheme shown below. Aminoalcohols can be selectively acylated at the amino group with an activated carboxyl derivative. Treatment with p-nitrophenyl chloroformate, and coupling with an amine is carried out as described above to give the target compounds.

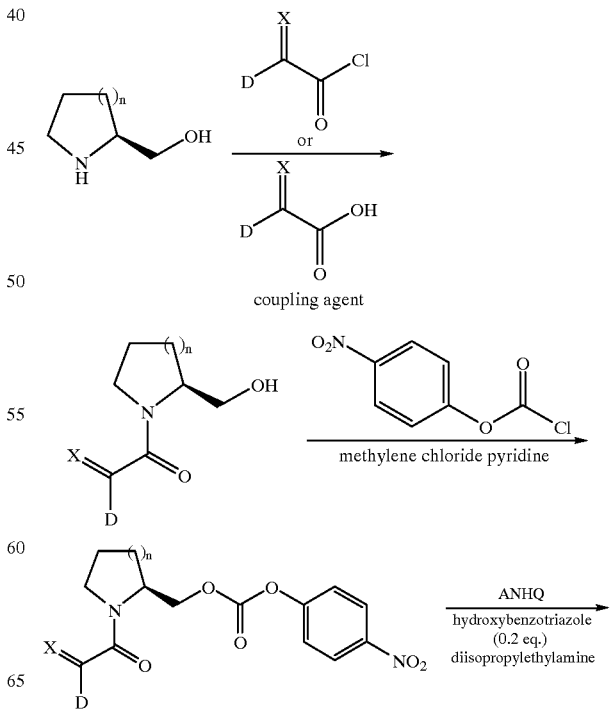

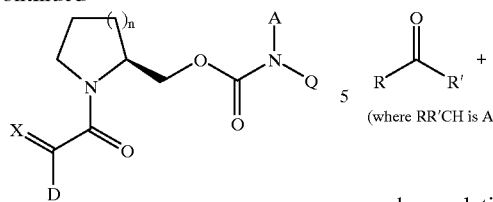

Intermediates used to prepare secondary and tertiary alkyl-substituted carbamrates can be prepared by Grignard additions to aldehydes and esters as shown below.

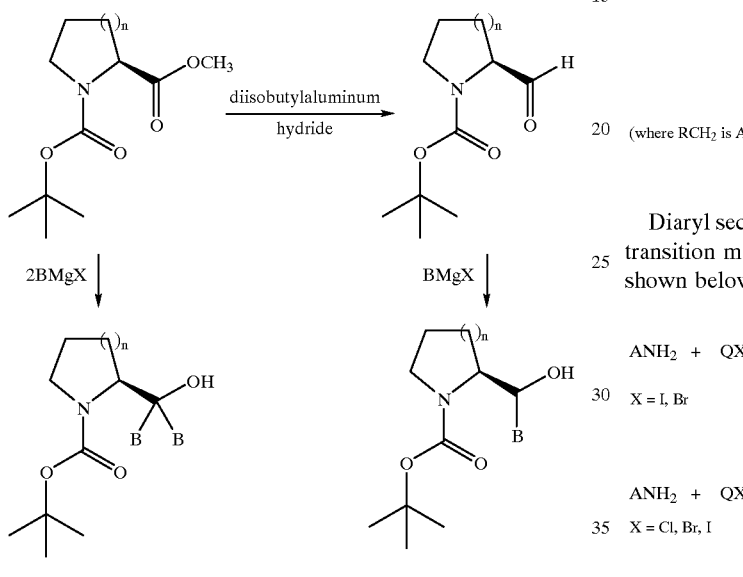

where B = L

For differently-substituted compounds (i.e., where B and L are different), the mono-alkylated intermediate can be re-oxidized and treated with a second Grignard reagent.

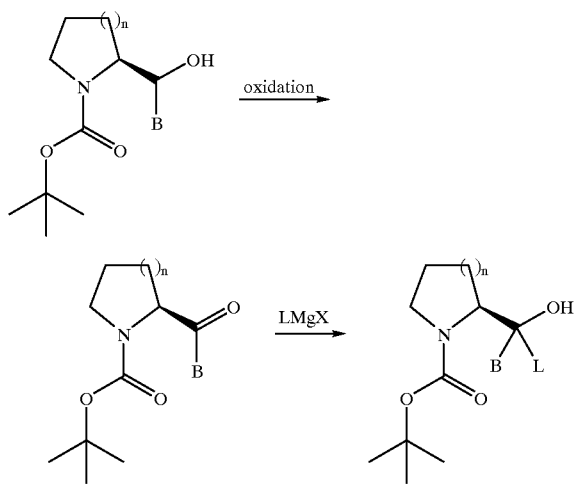

The secondary amine interinediates utilized in this invention can be prepared either by reductive amination of an aldehyde with a prirnary amine as shown below:

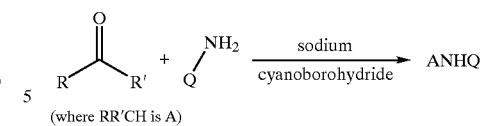

(where RR'CH is A)

or by acylation of an amine, followed by reduction of the amide with diborane or lithium aluminum hydride:

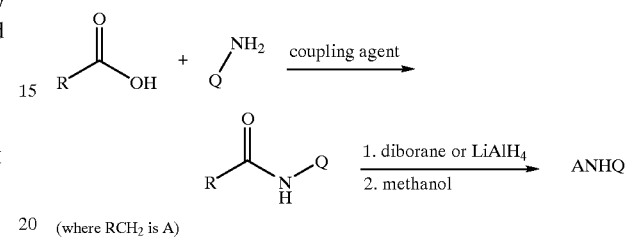

(where RCH$_2$ is A)

Diaryl secondary amine intermediates can be prepared by transition metal mediated coupling reactions such as those shown below.

ANH$_2$ + QX $\xrightarrow{\text{palladium catalyst}}$ ANHQ

X = I, Br or

ANH$_2$ + QX $\xrightarrow{\text{copper salt}}$ ANHQ

X = Cl, Br, I where QX is appropriately activated by electron withdrawing substituents.

Enamine intermediates may be prepared by condensation of primary amines with aldehydes and ketones as shown below.

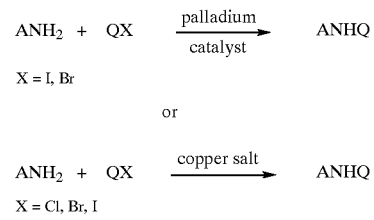

(where 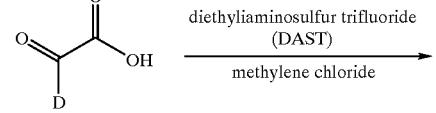 is A)

The 2,2-difluoroacetic acids are synthesized by fluorination of the parent keto compound with diethylaminosulfurtrifluoride. The N,N-diethylamide is obtained as the major product, but it is easily converted to the desired acid by alkaline hydrolysis.

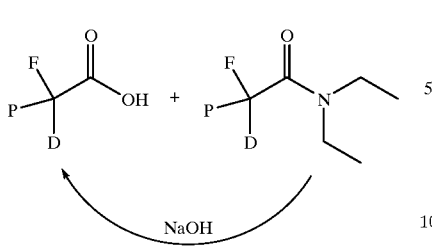

The 2,2-difluoroacetic acids are converted to the corresponding acid chlorides using oxalyl chloride and catalytic dimethylformamide in methylene chloride.

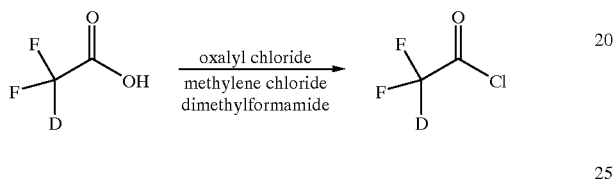

The diamides of this invention are best prepared according to the general scheme shown below. N-Boc-proline methyl ester is reduced to the corresponding aldehyde and coupled with the appropriate Wittig reagent to give the methyl acrylate which is then reduced to the 3-pyrrolidinylpropionate. The methyl ester is hydrolyzed to the acid, which is coupled to the secondary amines described above. Removal of the Boc protecting group and coupling to the keto- or difluoroacids are carried out as described above for the carbamate examples.

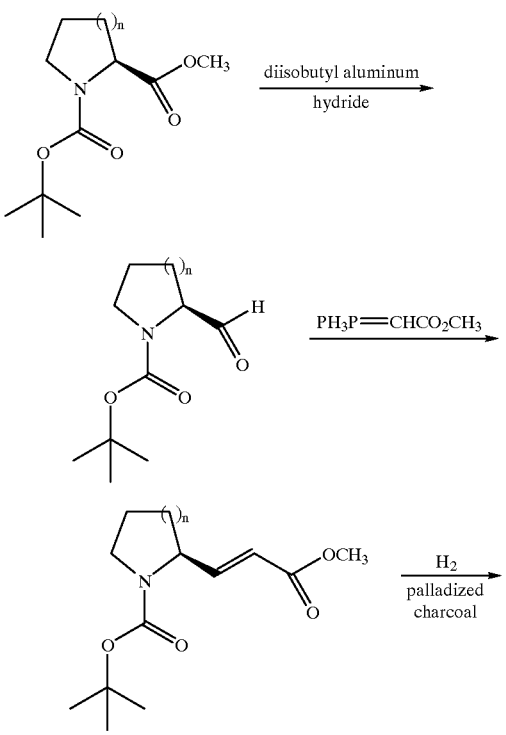

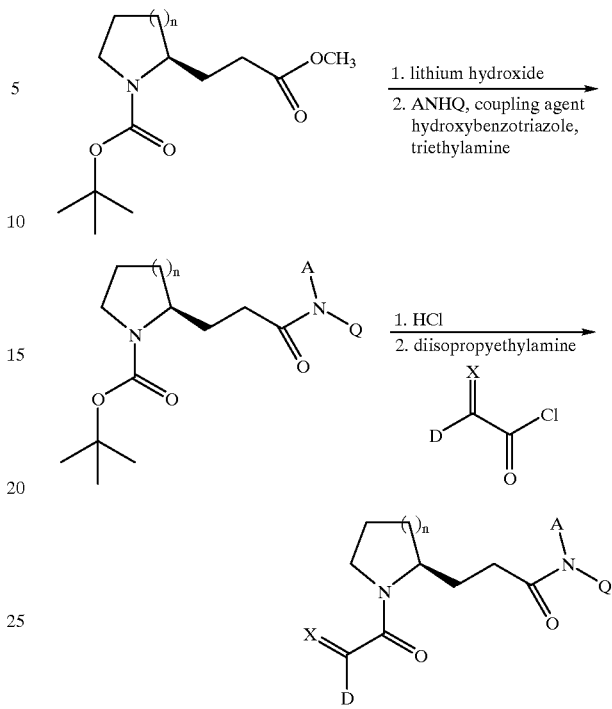

Alternatively, the aldehydes in the scheme shown above can be prepared by oxidation of the corresponding alcohols.

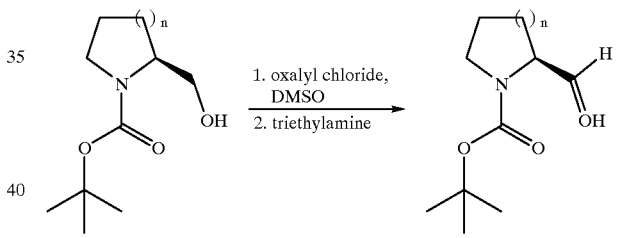

PREPARATION OF INTERMEDIATES
N-t-Boc-L-pyrrolidinylmethyl-p-nitrophenylcarbonate A stirred solution of L-prolinol (10.21 g, 100 mmoles) in methylene chloride (75 mL) at room temperature (rt) was treated with t-butyl pyrocarbonate (22.03 g, 1 equiv.) at such a rate as to cause only a gentle reflux. Following addition, the mixture was stirred at rt for 1.5 h and then the solvent was removed by evaporation. The residue was dried in vacuo for several hours and then dissolved in dry methylene chloride (150 mL). The solution was cooled to 0° C. and treated with p-nitrophenylchloroformate (20.37 g, 1 equiv.) and pyridine (8.2 mL, 1 equiv.). After stirring at rt overnight the solvent was removed by evaporation and the residue dissolved as far as possible in ether (250 mL). The solid pyridine hydrochloride was removed by filtration and the filtrate washed with water, 2% phosphoric acid, water, and brine, dried over sodium sulfate and evaporated to give a thick, pale-yellow oil (27.90 g, 75%) that was pure enough by NMR to carry on without further purification.

$^1$H-NMR δ (CDCl$_3$) 1.46 (9H, s), 1.99 (4H, m), 3.41 (2H, m), 4.07 and 4.22 (1H, 2×m), 4.31 (2H, d), 7.39 (2H, d), 8.25 (2H, d).

Mass Spec. (ESI): 367.4 (MH)$^+$.

N-t-Boc-(±)-piperidinylmethyl-p-nitrophenylcarbonate

This was prepared as described in the prior preparation, from racemic 2-hydroxymethylpiperidine giving 23.62 g of the product (95%) as a tan solid.

$^1$H-NMR δ (CDCl$_3$) 1.43 (11H, m and s), 1.68 (4H, m), 2.83 (1H, t), 4.02 (1H, brd), 4.31 (1H, ABq), 4.44 (1H, t), 4.66 (1H, m), 7.40 (2H, d), 8.24 (2H, d).

Mass Spec. (ESI): 381.3 (MH)$^+$.

N-Trimethylpyruvyl-L-pyrrolidinylmethanol

A stirred solution of trimethylpyruvic acid (1.37 g, 10.50 mmoles), N-hydroxybenzotriazole (HOBt) (1.61 g, 1 equiv.) and L-prolinol (1.24 mL, 1.2 equiv.) in tetrahydrofuran (100 mL) at 0° C. was treated with 0.5M dicyclohexylcarbodiimide in methylene chloride (25.2 mL, 1.2 equiv.). The mixture was stirred at rt overnight and then the solid urea by-product was removed by filtration. The filtrate was concentrated in vacuo and the residue dissolved in 1:1 ether/ethyl acetate. The solution was washed with water and brine, dried over sodium sulfate and evaporated to give a white, waxy solid (1.48 g, 66%).

$^1$H-NMR δ (CDCl$_3$) 1.03 (9H, s), 1.72 (1H, m), 1.91 (2H, m), 2.04 (1H, m), 3.45 (1H, ABq), 3.51 (1H, ABq), 3.63 (1H, ABq), 3.76 (1H, m), 4.02 (1H, ABq).

Mass Spec. (ESI): 214.3 (MH)$^+$.

N-Trimethylpyruvyl-L-pyrrolidinylmethyl-p-nitrophenylcarbonate

A stirred solution of the alcohol from Example 3 (242.3 mg, 1.136 mmoles) in methylene chloride (10 mL) at 0° C. was treated with p-nitrophenyl chloroformate (274.8 mg, 1.2 equiv.) and pyridine (0.11 mL, 1.2 equiv.). The mixture was stirred at rt overnight. Thin layer chromatography indicated ca. 30% unreacted starting material. More p-nitrophenyl chloroformate (114.5 mg, 0.5 equiv.) and pyridine (0.046 mnL, 0.5 equiv.) were added. Stirring was continued overnight at rt. The mixture was then concentrated in vacuo and the residue dissolved in 1:1 ether/ethyl acetate. The solution was washed with 2% phosphoric acid, water and brine, dried over sodium sulfate and evaporated. The residue was chromatographed on silica gel, eluting with 35% ethyl acetate/hexane, to give the product as a white, waxy solid (288 mg, 67%).

$^1$H-NMR δ (CDCl$_3$) 1.28 (9H, d), 1.95 (2H, m), 2.04 (1H, m), 2.12 (1H, m), 3.42 (2H, m), 4.33 (1H, m), 4.51 (2H, m), 7.40 (2H, d), 8.29 (2H, d).

Mass Spec. (ESI): 379.3 (MH)$^+$.

3-(3-Pyridyl)propylammonium p-toluenesulfonate

A stirred solution of 3-(3-pyridyl)propanol (3.5 mL, 27.12 mmoles) in methylene chloride (15 mL) at 0° C. was treated with p-toluenesulfonyl chloride (6.7219 g, 1.3 equiv.) and diisopropylethylamine (6.14 mL, 1.3 equiv.). After 10 minutes, the mixture was warmed to room temperature. After a further 4 hours, the solvent was removed under reduced pressure and the residue partitioned between ethyl acetate and water. The organic phase was washed with brine, dried over sodium sulfate and evaporated. the residue was chromatographed on silica, eluting with ethyl acetate, to give a thick, pale-yellow oil which was immediately dissolved in saturated ammonialmethanol (165 mL). This was left to stand at room temperature for 5 days at which time the solvent was removed under reduced pressure. The residue was dried under high vacuum and then dissolved as far as possible in ether (150 mL). The resulting solid product was collected by filtration, washed with ether, and dried in vacuo (6.3051 g, 76%).

$^1$H-NMR δ (DMSO-d$_6$) 1.84 (m, 2H), 2.28 (s, 3H), 2.64 (t, 2H), 2.80 (t, 2H), 7.11 (d, 2H), 7.35 (ABq, 1H), 7.49 (d, 2H), 7.63 (m, 1H), 7.69 (br, 3H), 8.41 (m, 2H).

3-(3-Pyridyl)propyl-3-phenylpropylamine

A stirred mixture of 3-(3-pyridyl)propionaldehyde (4.40 g, 32.5 mmoles) and 3-phenylpropylamine (5.30 g, 1.2 equiv.) in methanol at rt was treated with sodium cyanoborohydride (1 g, 0.5 equiv.). After 1 h at rt the mixture was further treated with solid potassium hydroxide (3.6 g, 2 equiv.) and stirring was continued for 2 h. The resulting mixture was partitioned between brine and ether. The aqueous layer was extracted with ether and the combined ether extracts were extracted with 6N HCl (3×). These aqueous extracts were basified with solid potassium hydroxide and extracted with ether (3×), dried over sodium sulfate and concentrated in vacuo. The residue was distilled under high vacuum to give the product as a colorless oil (2.44 g, 30%), b.p. ca. 162° C./0.5 mm Hg.

$^1$H-NMR δ (CDCl$_3$) 1.77 (4H, m), 2.42 (1H, m), 2.63 (8H, m), 7.18 (4H, m), 7.26 (2H, m), 7.49 (1H, t), 8.43 (2H, m).

The following compounds were prepared essentially as described for the previous preparation:

3-(3-Pyridyl)propyl-4-phenylbutylamine $^1$H-NMR δ (CDCl$_3$) 8.39 (br s, 1 H); 7.44 (d, 1 H); 7.29–7.14 (m, 7 H); 2.89–2.77 (m, 4 H); 2.66–2.57 (m, 4 H); 2.17 (br s, 1 H); 1.75 (q, 2 H).

3-(3-Pyridyl)propyl-2-phenylethylamine $^1$H-NMR δ (CDCl$_3$) 8.41 (m, 1 H); 7.45 (d, 1 H); 7.31–7.13 (m, 7 H); 2.95–2.71 (m, 2 H); 2.68–2.54 (m, 4 H); 2.47 (t, 2 H); 2.05 (m, 1 H); 1.67–1.41 (m, 4 H).

3-(3-Pyridyl)propyl-benzylamine $^1$H-NMR δ 8.44 (m, 1 H); 7.44 (d, 1 H); 7.35–7.19 (m, 7 H); 3.77 (s, 2 H); 2.68 (m, 4 H); 1.82 (q, 2 H); 1.78 (br s, 1 H).

4-(3-Pyridyl)butyl-4-phenylbutylamine $^1$H-NMR δ 8.41 (m, 0.5 H); 7.24 (m, 1.5 H); 7.34–7.07 (m, 7 H); 2.80 (m, 2 H); 2.66 (m, 8 H); 1.88 (m, 2 H); 1.78–1.42 (m, 5 H).

4-(3-Pyridyl)butyl-3-phenylpropylamine $^1$H-NMR δ 8.41 (m, 1 H); 7.23 (m, 1 H); 7.34–7.07 (m, 7 H); 2.80 (m, 2 H); 2.61 (t, 4 H); 2.53 (t, 4 H); 1.83–1.47 (br m, 7 H).

4-(3-Pyridyl)butyl-2-phenylethylamine $^1$H-NMR δ 8.41 (m, 1 H); 7.45 (d, 1 H); 7.31–7.13 (m, 7 H); 2.95–2.71 (m, 2 H); 2.68–2.54 (m, 4 H); 2.47 (t, 2 H); 2.05 (m, 1 H); 1.67–1.41 (m, 4 H).

4-(3-Pyridyl)butyl-benzylamine $^1$H-NMR δ 8.43 (m, 1.5 H); 7.42 (m, 0.5 H); 7.38–7.17 (m, 7 H); 3.49 (s, 2 H); 2.53 (q, 2 H); 2.39 (q, 2 H); 1.61–1.41 (m, 5 H).

2-(3-Indolyl)ethyl-2-phenylethylamine $^1$H-NMR δ 7.97 (bs, 1 H); 7.64 (d, J=8.2 Hz, 1 H); 7.38 (d, J=8.3 Hz, 1 H); 7.29–7.07 (m, 7 H); 6.95 (d, J=2.4 Hz, 1 H); 2.99 (s, 4 H); 2.92 (t, J=7.0 Hz, 2 H); 2.80 (t, J=6.8 Hz, 2 H).

Mass Spec. (ESI): 265.2 (MH)$^+$.

(E) Ethyl 4-carboxycinnamate

4—Carboxybenzaldehyde (1.0 g) was added to sodium hydride (170 mg) in 100 mL tetrahydrofuran at 0° C. In a separate flask, triethyl phosphonoacetate (1.60 mL) was added to sodium hydride (200 mg) in 100 mL tetrahydrofuran at 0° C. The phosphonate anion solution was cannulated into the slurry of the carboxylate anion and the resulting thick white slurry was stirred for 16 hours. Water (50 mL) was added followed by concentrated hydrochloric acid until the pH was 1. The precipitate was collected by filtration, dissolved in ether and dried with magnesium sulfate. Evaporation under reduced pressure gave the product (1.47 g; 100%) as a white solid.

$^1$H-NMR δ (CDCl$_3$) 8.13 (d, J=8.2 Hz, 2 H); 7.73 (d, J=16.3 Hz, 1 H); 7.64 (d, J=8.0 Hz, 2 H); 6.52 (d, J=16.1 Hz, 1 H); 4.29 (q, J=7.3 Hz, 2 H); 1.35 (t, J=7.5 Hz, 3 H).

Ethyl 3-(4-carboxyphenyl) propionate

A solution of (E) ethyl 4carboxycinnamate in ethanol was treated with 20% palladium hydroxide on carbon (500 mg). The mixture was stirred under a hydrogen atmosphere for 2 days and was then filtered through celite to remove inorganics. Evaporation gave ethyl 3-(4-carboxyphenyl) propionate as a white solid (1.19 g; 80% yield).

$^1$H-NMR δ (CDCl$_3$) 8.04 (d, J=8.2 Hz, 2 H); 7.31 (d, J=8.1 Hz, 2 H); 4.13 (q, J=7.1 Hz, 2 H); 3.04 (t, J=7.7 Hz, 2 H); 2.66 (t, J=7.7Hz, 2 H); 1.23 (t, J=7.3 Hz, 3 H).

Benzyl 4-(3-hydroxypropyl)benzoate

A stirred solution of ethyl 3-(4-carboxyphenyl) propionate in 200 mL tetrahydrofuran was treated with lithium aluminum hydride (400 mg). After 4 hours, excess hydrochloric acid was added and the mixture was extracted with ether. The organic layer was dried with magnesium sulfate and the solvent was removed in vacuo. This residue was dissolved in 2 mL dimethylformamide and to this was added benzyl bromide (700 μL) and potassium carbonate (1.0 g). The reaction was stirred for 16 hours and then diluted with water (20 mL). The solution was saturated with sodium chloride and extracted with ethyl acetate. The organic layer was dried with magnesium sulfate and purified by silica gel chromatography to give the product as a clear oil (385 mg, 27%).

1H-NMR δ (CDCl$_3$) 8.00 (d, J=8.6 Hz, 2 H); 7.48–7.30 (m, 5 H); 7.27 (d, J=8.6 Hz, 2 H); 5.35 (s, 2 H); 3.68 (t, J=7.1 Hz, 2 H); 2.77 (t, J=7.4 Hz, 2 H); 1.90 (m, 2 H). The product was oxidized by either Dess-Martin periodinane or Swern methods to give the corresponding aldehyde which could be used in reductive aminations according to the procedure described for 3-(3-Pyridyl)-propyl-3-phenylpropylamine. The amine resulting from reductive amination with 3-(3-pyridyl)propyl amine was not fully characterized but showed Mass Spec. (ESI): 389.3 (MH)$^+$.

3-(3-Pyridyl)propyl-4-(3,4-dimethoxyphenyl)butylamine

A stirred solution of 3-(3-pyridyl)propylamine (517.8 mg, 1.679 mmoles), 4-(3,4-dimethoxyphenyl)butanoic acid (376.5 mg, 1 equiv.) and N-hydroxysuccinimide (193.2 mg, 1.1 equiv.) in methylene chloride (15 mL) at 0° C. was treated with EDC hydrochloride (353.1 mg, 1.1 equiv.). The mixture was allowed to warm to room temperature after 10 minutes. Stirring was continued for 16 hours and then the solvent was removed under reduced pressure. The residue was partitioned between ethyl acetate and water. The aqueous phase was re-extracted with ethyl acetate. The combined organic phases were washed with water and brine, dried over sodium sulfate and evaporated to give a colorless oil. This crude amide was dissolved in dry tetrahydrofuran (5 mL) under argon. The solution was cooled to 0° C. and then treated with 1 M borane-tetrahydrofuran complex (7.0 mL, 4 equiv.). The mixture was heated at reflux for 16 hours and then cooled to room temperature. Dry methanol (10 mL) was added carefully to the stirred mixture to avoid foaming. The resulting solution was evaporated under reduced pressure and the residue dissolved in dry methanol (20 mL). The mixture was heated at reflux for 4 hours and then evaporated. The crude amine was carried on without purification.

$^1$H-NMR δ (CDCl$_3$) 1.61 (m, 6H), 2.12 (br, 1H), 2.60 (m, 8H), 3.85 (s, 3H), 3.86 (s, 3H), 6.71 (m, 3H), 7.18 (ABq, 1H1), 7.47 (d, 1H), 8.41 (m, 2H).

The following compounds were prepared essentially as described for the previous preparation:

3-(3-Pyridyl)propyl-3-(3,4,5-trimethoxyphenyl)propylamine $^1$H-NMR δ (CDCl$_3$) 1.80 (m, 4H), 2.63 (m, 8H), 3.80 (s, 3H), 3.82 (2×s, 6H), 6.39 (d, 2H), 7.18 (ABq, 1H), 7.47 (m, 1H), 8.40 (m, 2H).

3-(3-Pyridyl)propyl-3-(3-methoxyphenyl)propylamine $^1$H-NMR δ (CDCl$_3$) 1.83 (m, 4H), 2.64 (m, 8H), 3.75 (s, 3H), 6.75 (m, 3H), 7.17 (m, 2H), 7.44 (m, 1H), 8.37 (m, 2H).

3-(3-Pyridyl)propyl-3-(4-methoxyphenyl)propylamine $^1$H-NMR δ (CDCl$_3$) 1.78 (m, 4H), 2.57 (m, 8H), 3.72 (s, 3H), 6.77 (ABq, 2H), 7.06 (ABq, 2H), 7.16 (ABq, 1H), 7.42 (m, 1H), 8.39 (m, 2H).

3,4,5-Trimethoxyphenyl-2-oxoacetyl chloride

A stirred suspension of 3',4',5'-trimethoxyphenyl-2-oxoacetic acid (1.60 g, 6.66 mmoles) in dry methylene chloride (26 mL) at rt was treated with 2M oxalyl chloride in methylene chloride (14 mL, 4 equiv.) and dry dimethylformamide (1 drop). After 3 h the solvents were evaporated. The residue was flushed with dry imethylene chloride (3×50 mL) and dried in vacuo for 2 h during which time a solid formed. The crude acid chloride was carried on without further purification.

2,2-Difluoro-(3,4,5-trimethoxyphenyl)acetic acid.

To a stirred solution of 3,4,5-trimethoxyphenyl-2-oxoacetic acid (3.81 g, 15.8 mmol) in anhydrous methylene chloride (30 mL) at room temperature was added diethylaminosulfurtrifluoride (DAST) (20.4 g, 127 mmol) under nitrogen and the mixture was stirred overnight. The mixture was then cooled in an ice bath and excess DAST was quenched by dropwise addition of water. Ethyl acetate (300 mL) was added and the organic layer was washed with saturated aqueous sodium bicarbonate (2×100 mL) followed by water (100 mL). The residue obtained after drying and evaporation was purified by silica gel chromatography, eluting with hexane/ethyl acetate (9:1 to 7:3), to give the N,N-diethylamide derivative (2.10 g, 6.62 mmol, 42%) as a pale yellow solid. $^1$H-NMR: 6.77 (s, 2H), 3.88 (s, 9H), 3.45 (q, J=7.0 Hz, 2H), 3.25 (q, J=7.0 Hz, 2H), 1.20 (t, J=7.0 Hz, 3H), 1.10 (t, J=6.9 Hz, 3H). Bicarbonate washing after acidification and extractive work up with ethyl acetate gave the crude title compound. Purification by reversed phase column (C18) chromatograhy eluting with water/methanol/trifluoroacetic acid (69.9:30:0.1) gave the pure 2,2-difluoro acid (0.616 g, 2.34 mmol, 15%) as a white solid. $^1$H-NMR: 6.85 (s, 2H), 3.90 (s, 6H), 3.89 (s, 3H). Anal. C: 50.59, H: 4.72, F: 14.24 (found), C: 50.39, H: 4.61, F: 14.49 (calcd). The N,N-diethylamide (2.00 g, 6.30 mmol) obtained above was hydrolyzed to the title acid by heating a solution in ethanol (5 mL) with 10% sodium hydroxide (13 mL) at reflux for 4 h. Acidification followed by extractive work up with ethyl acetate gave the crude acid which was purified as described above to give 1.51 g of the title compound as a white solid.

2,2-Difluoro-3,4,5-trimethoxyphenylacetyl chloride

This was prepared as described above for 3,4,5-trimethoxypbenyl-2-oxoacetyl chloride from the corresponding carboxylic acid and was used without chromatographic purification.

N-t-Butyloxycarbonyl-L-pyrrolidinylmethyl-[N',N'-3-(3-pyridyl) propyl-3-phenylpropylamino]carbamate A stirred solution of 3-(3-pyridyl)propyl-3-phenylpropylamine (342.5 mg, 1.346 mmoles) and N-Boc-L-prolinyl-p-nitrophenylcarbonate (612.2 mg, 1.24 equiv.) in methylene chloride (7 mL) at rt was treated with N-hydroxybenzotriazole (37 mg, 0.2 equiv.) and diisopropylethylamine (0.235 mL, 1 equiv.). After stirring overnight at rt, the mixture was diluted with ethyl acetate and the solution was washed with 1M sodium hydroxide (2×), water and brine, dried over sodium sulfate, and concentrated in vacuo. The residue was chromatographed on silica gel, eluting with ethyl acetate, to give the product as a pale-yellow oil (500.6 mg, 77%).

¹H-NMR δ (CDCl₃) 1.42 (9H, s), 1.83 (8H, m), 2.58 (4H, brt), 3.27 (6H, m), 4.04 (3H, m), 7.17 (4H, m), 7.25 (2H, m), 7.50 (1H, m), 8.42 (2H, brs). Mass Spec. (ESI): 482.6 (MH)⁺.

The following compounds were prepared essentially as described for the previous preparation:

N-t-Butyloxycarbonyl-L-pyrrolidinylmethyl-N'-3-pyridylmethylcarbamate

¹H-NMR δ (CDCl₃) 1.43 (9H, s), 1.82 (4H, m), 3.33 (2H, brs), 4.10 (3H, m), 4.38 (2H, d), 5.22 (1H, br), 7.24 (1H, ABq), 7.60 (1H, d), 8.48 (2H, brs).

N-t-Butyloxycarbonyl-L-pyrrolidinylmethyl-N'-2-phenylethylcarbamate

¹H-NMR δ (CDCl₃) 1.42 (9H, s), 1.81 (4H, m), 2.78 (2H, t), 3.28 (2H, m), 3.40 (2H, m), 3.95 (2H, m), 4.10 (1H, m), 4.77 (1H, br), 7.21 (5H, m).

N-t-Butyloxycarbonyl-L-pyrrolidinylmethyl-[N',N'-3-(3-pyridyl) propyl-benzylamino]carbamate ¹H-NMR δ (CDCl₃) 8.41 (d, 0.5 H); 8.38 (s, 0.5 H); 7.43 (m, 1 H); 7.21 (m, 7H); 4.17 (m, 2 H); 3.91 (m, 1 H); 3.33 (br s, 2 H); 3.20 (br s, 2 H); 2.55 (m, 2 H); 1.80 (br m, 6 H); 1.40 (s, 9 H).

N-t-Butyloxycarbonyl-L-pyrrolidinylmethyl-[N',N'-3-(3-pyridyl) propyl-2-phenylethylamino]carbamate ¹H-NMR δ (CDCl₃) 8.41 (m, 1 H); 7.43 (m, 1 H); 7.21 (m, 7 H); 4.17 (m, 2 H); 3.91 (m, 1 H); 3.30 (br m, 6 H); 2.81 (d, 2 H); 2.57 (d, 2 H); 1.81 (m, 6 H); 1.42 (s, 9 H).

N-t-Butyloxycarbonyl-L-pyrrolidinylmethyl-[N',N'-3-(3-pyridyl) propyl-4-phenylbutylamino]carbamate ¹H-NMR δ (CDCl₃) 8.41 (m, 1 H); 7.43 (m, 1 H); 7.20 (m, 7 H); 4.50 (m, 1 H); 4.15 (m, 3 H); 3.41 (m, 2 H); 3.19 (m, 2 H); 2.81 (m, 3 H); 2.59 (m, 2 H); 1.79 (m, 2H); 1.62 (m, 10 H); 1.41 (s, 9H).

N-t-Butyloxycarbonyl-L-pyrrolidinylmethyl-[N',N'-4-(3-pyridyl) butyl-2-phenylethylamino]carbamate ¹H-NMR δ (CDCl₃) 8.42 (m, 1 H); 7.43 (m, 1 H); 7.20 (m, 7 H); 4.20 (m, 2 H); 3.87 (m, 1 H); 3.26–2.95 (m, 6 H); 2.79–2.43 (br m, 4 H); 1.84–1.63 (br m, 8 H); 1.41 (s, 9 H).

N-t-Butyloxycarbonyl-L-pyrrolidinylmethyl-[N',N'-4-(3-pyridyl) butyl-4-phenylbutylamino]carbamate ¹H-NMR δ (CDCl₃) 1.41 (9H, s), 1.57 (6H, m), 1.81 (4H, m), 2.60 (4H, brt), 3.21 (6H, m), 3.90 (1H, m), 3.97 (2H, m), 4.13 (1H, m), 7.19 (6H, m), 7.47 (1H, d), 8.41 (2H, brs).

N-t-Butyloxycarbonyl-L-pyrrolidinylmethyl-[N',N'-4-(3-pyridyl) (propyl-3-(m-methoxyphenyl)propylamino] carbamate ¹H-NMR δ (CDCl₃) 1.42 (s, 9H), 1.81 (m, 8H), 2.58 (m, 4H), 3.23 (m, 6H), 3.79 (s, 3H), 4.04 (m, 3H), 6.75 (m, 3H), 7.20 (m, 2H), 7.49 (brt, 1H), 8.42 (brs, 2H).

Mass Spec. (ESI): 512.42 (MH)⁺.

N-t-Butyloxycarbonyl-L-pyrrolidinylmethyl-[N',N'-4-(3-pyridyl) propyl-3-(p-methoxyphenyl)propylamino] carbamate ¹H-NMR δ (CDCl₃) 1.45 (s, 9H), 1.82 (m, 8H), 2.57 (m, 4H), 3.23 (m, 6H), 3.77 (s, 3H), 4.03 (m, 3H), 6.81 (d, 2H), 7.06 (brd, 2H), 7.21 (ABq, 1H), 7.48 (brt, 1H), 8.42 (brs, 2H).

Mass Spec. (ESI): 512.41 (MH)⁺.

N-t-Butyloxycarbonyl-L-pyrrolidinylmethyl-[N',N'-4-(3-pyridyl) propyl-3-(3,4,5-trimethoxyphenyl)propylamino] carbamate ¹H-NMR δ (CDCl₃) 1.43 (s, 9H), 1.82 (m, 8H), 2.55 (m, 4H), 3.28 (m, 6H), 3.79 (s, 3H), 3.81 (s, 3H), 4.02 (m, 3H), 6.36 (brs, 2H), 7.19 (ABq, 1H), 7.44 (m, 11H), 8.41 (brs, 2H).

Mass Spec. (ESI): 572.46 (MH)⁺.

N-t-Butyloxycarbonyl-L-pyrrolidinylmethyl-[N',N'-4-(3-pyridyl) ropyl-4-(3,4-dimethoxyphenyl)butylamino] carbamate ¹H-NMR δ (CDCl₃) 1.43 (s, 9H), 1.53 (m, 4H), 1.81 (m, 6H), 2.54 (m, 4H), 3.22 (m, 6H), 3.82 (s, 3H), 3.84 (s, 3H), 4.07 (m, 3H), 6.66 (brs, 2H), 6.75 (m, 1H), 7.19 (ABq, 1H), 7.46 (m, 1H), 8.41 (brs, 2H).

Mass Spec. (ESI): 556.44 (MH)⁺.

N-t-Butyloxycarbonyl-(±)-piperidinylmethyl-[N',N'-3-(3-pyridyl) propyl-3-phenylpropylamino]carbamate ¹H-NMR δ (CDCl₃) 1.42 (11H, m and s), 1.54 (4H, m), 1.82 (4H, m), 2.56 (4H, m), 2.81 (1H, q), 3.22 (4H, m), 3.97 (2H, brd), 4.12 (1H, ABq), 4.18 (1H, m), 4.44 (1H, br), 7.17 (4H, m), 7.22 (2H, t), 7.45 (1H, brd), 8.42 (2H, brs).

N-t-Butyloxycarbonyl-(±)-piperidinylmethyl[N',N'-3-(3-pyridyl) propyl-benzylamino]carbamate ¹H-NMR δ (CDCl₃) 8.41 (d, 0.5 H); 8.38 (s, 0.5 H); 7.42 (br t, 1 H); 7.21 (m, 7 H); 4.42 (m, 3 H); 4.23 (m, 1 H); 4.17 (m, 4 H); 3.22 (m, 2 H); 2.81 (m, 1 H); 2.50 (m, 2 H); 1.80 (m, 2 H); 1.55 (br s, 4 H); 1.41 (s, 9 H).

N-t-Butyloxycarbonyl-(±)-piperidinylmethyl-[N',N'-3-(3-pyridyl) propyl-2-phenylethylamino]carbamate ¹H-NMR δ (CDCl₃) 8.41 (s, 1 H); 7.43 (br t, 1 H); 7.21 (m, 7 H); 4.12 (m, 2 H); 3.27 (m, 5 H); 2.60 (m, 4H); 1.81 (br s, 6 H); 1.57 (br s, 4 H); 1.42 (s, 9 H).

N-t-Butyloxycarbonyl-(±)-piperidinylmethyl-[N',N'-3-(3-pyridyl) propyl-4-phenylbutylamino]carbamate ¹H-NMR δ (CDCl₃) 8.41 (s, 1 H); 7.42 (m, 1 H); 7.20 (m, 7 H); 4.42 (m, 1 H); 4.15 (m, 2 H); 4.01 (m, 1 H); 3.21 (m, 4 H); 2.82 (br t, 1 H); 2.68 (br s, 4 H); 1.81 (m, 2 H); 1.55 (m, 10 H); 1.41 (s, 9 H).

(S)-2-(2-Methoxycarbonylvinyl)-piperidine-1-carboxylic acid t-butyl ester

A stirred solution of (S)-N-(t-butoxycarbonyl)-pipecolinic acid methyl ester (2.04 g, 8.39 mmol) in methylene chloride (75 mL) at −78° C. under nitrogen was treated with diisobutylaluminum hydride (1.0 M in toluene, 14.2mL, 14.2 mmol). After 1.25 h a second aliquot of diisobutylaluminum hydride (2.00 mL, 2.00 mmol) was added. The mixture was stirred for an additional 30 min. and then quenched by the addition of a 20% aqueous Rochelle's salt solution (100 mL) followed by vigorous stirring for 1 h. The aqueous layer was extracted with methylene chloride and the combined organic extracts were dried over magnesium sulfate, filtered, and concentrated. The crude aldehyde was dissolved in methylene chloride (100 mL) and treated with methyl (triphenylphosphoranylidene)acetate (4.00 g, 12.0 mmol). After 15 hours (h) the reaction mixture was concentrated and purified by flash chromatography to give the desired product (1.46 g, 65%).

¹H-NMR δ (CDCl₃) 1.35 (m, 2 H), 1.45 (s, 9 H), 1.62 (m, 2 H), 1.78 (m, 2 H), 2.80 (t, 1 H, J=11.6), 3.74 (s, 3 H), 3.98 (d, 1 H, J=13.1), 4.94 (s, 1 H), 5.81 (dd, 1 H, J=1.7, 15.9), 6.88 (dd, 1 H, J=4.0, 15.9).

(S)-2-(2-Methoxycarbonylvinyl)-pyrrolidine-1-carboxylic acid t-butyl ester

To a solution of oxalyl chloride (2.0M in methylene chloride, 9.60 mL, 19.2 mmol) in methylene chloride (100 mL) at −60° C. was added a solution of dimethyl sulfoxide (3.01 g, 38.6 mmol) in methylene chloride (10 mL) and the mixture was stirred for 5 min. A solution of (S)-(−)-1-(t-butoxycarbonyl)-2-pyrrolidinemethanol (3.08 g, 15.3 mmol) in methylene chloride (20 mL) was added dropwise over 5 min. After 30 min, triethylamine (12.8 mL, 91.8 mmol) was added and the reaction mixture was stirred at −60° C. for 15 min and then warmed to rt for a further 10 min. Water (50 mL) was added and the mixture extracted with methylene chloride. The combined organic extracts were dried over magnesium sulfate, filtered, and concentrated. The crude residue was dissolved in methylene chloride (100 mL) and treated with methyl (triphenylphosphoranylidene)acetate (1.4 eq). After 15 h the reaction mixture was concentrated and purified by silica gel chromatography to give the desired product (3.54 g, 90%).

$^1$H-NMR δ (CDCl$_3$) 1.41 (s, 9 H), 1.85 (m, 3 H), 2.06 (m, 1 H), 3.42 (m, 2 H), 3.73 (s, 3 H), 4.42 (m, 1 H), 5.82 (d, 1 H, J=15.4), 6.82 (m, 1 H).

(S)-2-(2-Methoxycarbonyl-ethyl)-piperidine-1-carboxylic acid t-butyl ester

To a solution of (S)-2-(2-methoxycarbonylvinyl)-piperidine-1-carboxylic acid t-butyl ester (1.46 g, 5.41 mmol) in 1:1 methanol:methylene chloride (40 mL) was added 10% palladized charcoal (0.129 g). The mixture was hydrogenated (59 psi) for 5.5 h. The catalyst was removed by filtration through a bed of celite and the solution concentrated in vacuo. Purification by silica gel chromatography provided the product (1.10 g, 75%).

$^1$H-NMR δ (CDCl$_3$) 1.44 (s, 9 H), 1.60 (m, 7 H), 2.11 (m, 1 H), 2.30 (m, 2 H), 2.73 (t, 1 H, J=13.5), 3.66 (s 3 H), 4.11 (m, 1 H), 4.24 (m, 1 H).

The following compound was prepared essentially as described for the previous preparation:

(S)-2-(2-Methoxycarbonyl-ethyl)-pyrrolidine-1-carboxylic acid t-butyl ester $^1$H-NMR δ (CDCl$_3$) 1.45 (s, 9 H), 1.65 (m, 2 H), 1.90 (m, 4 H), 2.32 (t, 2 H, J=7.9), 3.32 (m, 2 H), 3.66 (s, 3 H), 3.80 (m, 1 H).

N,N-(3-Phenylpropyl)-3-(3-pyridyl)propyl-2-[(S)-N'-t-butoxycarbonyl-2-piperidinyl]propionamide A solution of (S)-2-(2-methoxycarbonyl-ethyl)-piperidine-1-carboxylic acid t-butyl ester (0.544 g, 2.00 mmol) in tetrahydrofuran (15 mL) was treated with LiOH (1M, 15 mL). After 2.5 h the mixture was acidified with 1N HCl (pH 2) and extracted with methylene chloride. The combined organic extracts were dried over magnesium sulfate, filtered and concentrated. The crude product was dissolved in methylene chloride (10 mL) and cooled to 0° C. 3-(3-Pyridyl)propyl-3-phenylpropylamine (0.506 g, 1.99 mmol) in methylene chloride (5 mL) was added, followed by 1-(3-dimethylaminopropyl)3-ethyl cardodiimide (EDC) (0.414 g, 2.16 mmol), 1-hydroxybenzotriazole (0.292 g, 2.16 mmol), and triethylamine (0.560 mL, 4.02 mmol). The solution was allowed to warm to rt and stirred for 15 h. The reaction mixture was diluted with methylene chloride (100 mL). The organic layer was washed with 1N HCl, saturated sodium bicarbonate, and brine, then dried (MgSO$_4$), filtered, and concentrated in vacuo. Purification by flash chromatography yielded the product (0.755 g, 76%).

$^1$H-NMR δ (CDCl$_3$) 1.43 (s, 9 H), 1.56 (m, 4 H), 1.65 (m, 2 H), 1.85 (m, 5 H), 2.15 (m, 3 H), 2.60 (m, 4 H), 2.72 (m, 1 H), 3.22 (m, 2 H), 3.33 (m, 2 H), 3.95 (m, 1 H), 4.23 (m, 1 H), 7.22 (m, 5 H), 7.53 (dd, 1 H, J=5.3, 7.8), 7.97 (d, 1 H, J=7.8), 8.50 (m, 2 H).

Mass Spec. (ESI): 494 (MH)$^+$.

The following compound was prepared essentially as described for the previous preparation:

N,N-(3-Phenylpropyl)-3-(3-pyridyl)propyl-2-[(S)-N'-t-butoxycarbonyl-2-pyrrolidinyl]propionamide $^1$H-NMR δ (CDCl$_3$) 1.43 (s, 9 H), 1.65 (m, 2 H), 1.83 (m, 8 H), 2.20 (m, 2 H), 2.62 (m, 3 H), 2.72 (m, 1 H), 3.27 (m, 6 H), 3.82 (m, 1 H), 7.25 (m, 5 H), 7.75 (m, 1 H), 8.02 (m, 1 H), 8.52 (m, 2 H).

Mass Spec. (ESI): 480 (MH)$^+$.

EXAMPLES

Example 1

N-Trimethylpyruvyl-L-pyrrolidinylmethyl-[N',N'-3-(3-pyridyl)propyl-3-phenylpropylamino]carbamate

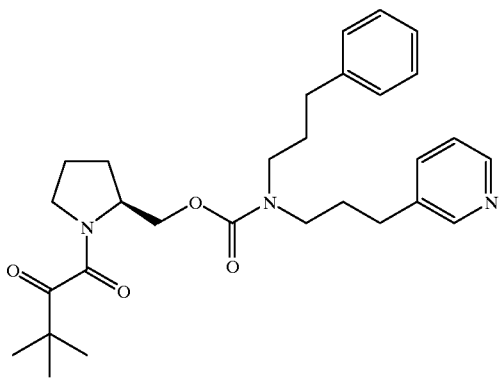

A mixture of 3-(3-pyridyl)-propyl-3-phenylpropylamine (0.38 g, 1.10 mmoles) and N-trimethylpyruvyl-L-prolinyi-p-nitrophenylcarbonate (0.46 g, 1.1 equiv.) in methylene chloride (2 mL) was stirred at rt over 4 days. The mixture was then washed with water, dried over magnesium sulfate and concentrated in vacuo. The residue was chromatographed on silica gel, eluting with ethyl acetate, to give the product as a thick oil (0.32 g, 59%).

$^1$H-NMR δ (CDCl$_3$) 1.23 (9H, d), 1.85 (8H, m), 2.58 (4H, brt), 3.24 (6H, m), 4.21 (2H, d), 4.37 (1H, m), 7.16 (4H, m), 7.23 (2H, m), 7.47 (1H, m), 8.42 (2H, brs).

Mass Spec. (ESI): 494.4 (MH)$^+$.

Example 2

N-Trimethylpyruvyl-L-pyrrolidinylmethyl-[N',N'-dibenzylamino]carbamate

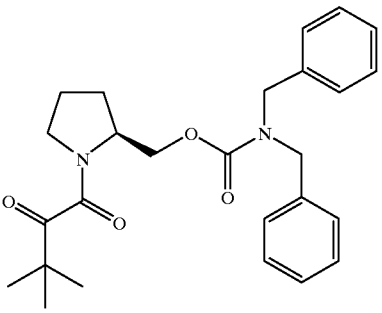

$^1$H-NMR δ (CDCl$_3$) 1.21 (s, 9H), 1.83 (m, 4H), 3.14 (m, 2H), 3.30 (m, 2H), 4.39 (brs, 4H), 4.48 (m, 3H), 7.28 (m, 10H).

Mass Spec. (ESI): 437.3 (MH)$^+$.

Example 3

N-Trimethylpyruvyl-L-pyrrolidinylmethyl-[N',N'-2-phenylethyl-benzylamino]carbamate

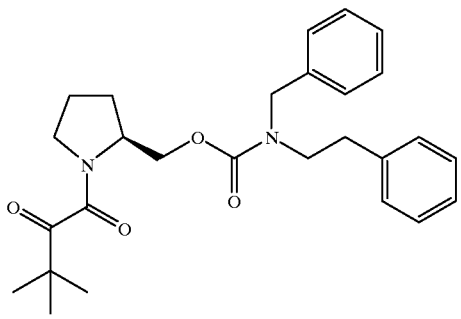

$^1$H-NMR δ (CDCl$_3$) 1.23 (m, 9H), 1.91 (m, 4H), 2.80 (2×t, 2H), 3.41 (m, 4H), 4.37 (m, 2H), 4.41 (brs, 1H), 7.21 (m, 10H).

Mass Spec. (ESI): 451.3 (MH)$^+$.

Example 4

N-Trimethylpyruvyl-L-pyrrolidinylmethyl-[N'-3-pyridylmethylamino]carbamate

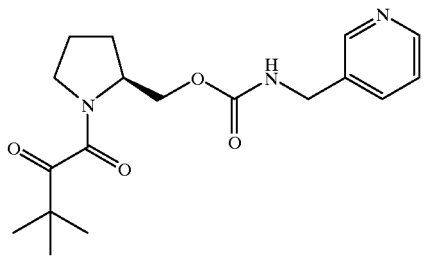

$^1$H-NMR δ (CDCl$_3$) 1.24 (9H, s), 1.93 (4H, m), 3.35 (2H, m), 4.22 (2H, ABq), 4.39 (3H, d and m), 5.37 (1H, br), 7.32 (1H, m), 7.86 (1H, m), 8.55 (2H, m).

Mass Spec. (ESI): 379.3 (MH)$^+$.

Example 5

N-Trimethylpyruvyl-L-pyrrolidinylmethyl-[N'-2-phenylethylamino]carbamate

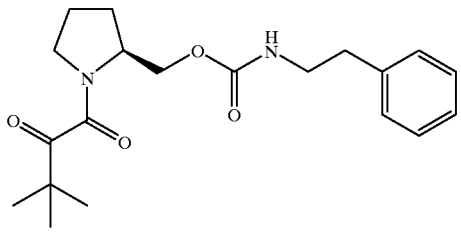

$^1$H-NMR δ (CDCl$_3$) 1.22 (s, 9H), 1.90 (m, 4H), 2.80 (t, 2H), 3.35 (m, 2H), 3.42 (q, 2H), 4.20 (d, 2H), 4.34 (m, 1H), 4.73 (m, 1H), 7.21 (m, 5H).

Mass Spec. (ESI): 361.4 (MH)$^+$.

Example 6

N-Trimethylpyruvyl-L-pyrrolidinylmethyl-[N'-3-phenylpropylamino]carbamate

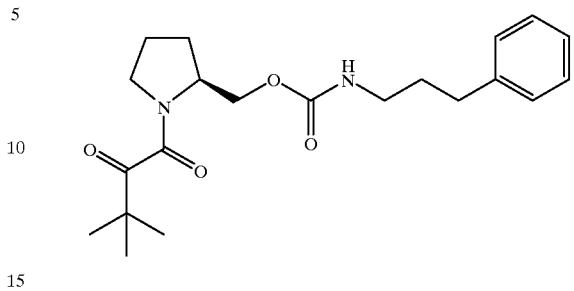

$^1$H-NMR δ (CDCl$_3$) 1.21 (s, 9H), 1.82 (m, 6H), 2.60 (t, 2H), 3.16 (m, 2H), 3.32 (m, 2H), 4.19 (d, 2H), 4.32 (m, 1H), 4.96 (m, 1H), 7.20 (m, 5H).

Mass Spec. (ESI): 375.4 (MH)$^+$.

Example 7

N-(3,4,5-Trimethoxyphenyl)oxalyl-L-pyrrolidinylmethyl-[N',N'-3-(3-pyridyl)propyl-3-phenylpropylamino]carbamate

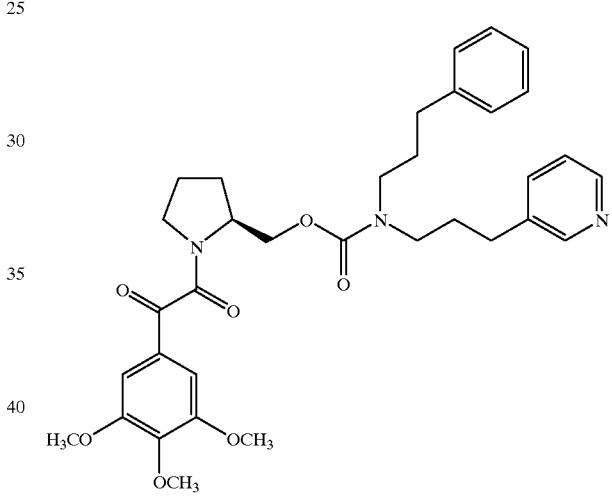

A solution of N-t-butyloxycarbonyl-L-pyrrolidinylmetbyl-[N',N'-3-(3-pyridyl)propyl-3-phenylpropylamino]carbamate (470.2 mg, 0.9763 mmoles) in methylene chloride (2 mL) was treated with 4M HCl in dioxane (2.5 mL). After 1 h the solvents were removed under vacuum. The residue was flushed with dry methylene chloride (3×25 mL), dried in vacuo for 1 h, and dissolved in dry methylene chloride (5 mL). To this was added a solution of 3,4,5-trimethoxyphenyl-2-oxoacetyl chloride (506.5 mg, 2 equiv.) in methylene chloride (5 mL), followed by diisopropylethylamine (0.51 mL, 3 equiv.). The mixture was stirred at rt overnight and then concentrated in vacuo. The residue was dissolved in 1:1 ethyl acetateiether and the solution washed with 1 M sodium hydroxide (2×), water, brine, dried over sodium sulfate and evaporated. The residue was chromatographed on silica, eluting with ethyl acetate, to give the product as a pale-yellow oil (561.8 mg, 95%).

$^1$H-NMR δ (CDCl$_3$) 1.83 (6H, m), 1.94 (2H, m), 2.54 (4H, m), 3.03 (1H, m), 3.22 (3H, m), 3.41 (1H, m), 3.59 (1H, m), 3.84 (9H, m), 4.22 (1H, m), 4.37 (1H, m), 4.50 (1H, m), 7.17 (4H, m), 7.21 (4H, d and m), 7.44 (1H, brt), 8.40 (2H, brs).

Mass Spec. (ESI): 604.6 (MH)$^+$.

The following compounds were prepared essentially as described for the previous examnple 7:

Example 8

N-(3,4,5-Trimethoxyphenyl)oxalyl-L-pyrrolidinylmethyl-[N'-3-pyridylmethylamino]carbamate

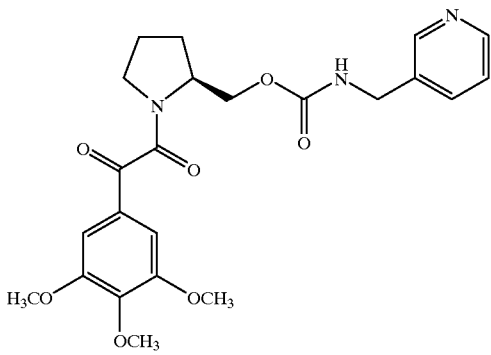

¹H-NMR δ (CDCl₃) 1.96 (m, 4H), 3.52 (m, 2H), 3.81 (m, 9H), 4.00 (m, 2H), 4.30 (d, 2H), 4.41 (m, 1H), 5.80 (brt, 1H), 7.20 (m, 3H), 7.49 (ABq, 1H), 8.41 (m, 2H).

Mass Spec. (ESI): 458.4 (MH)⁺.

Example 9

N-(3,4,5-Trimethoxyphenyl)oxalyl-L-pyrrolidinylmethyl-[N'-2-phenylethylamino]carbamate

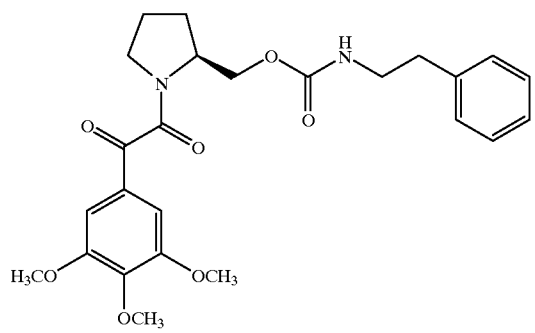

¹H-NMR δ (CDCl₃) 1.96 (m, 4H), 2.58 (t, 2H, rotamer A), 2.79 (t, 2H, rotamer B), 3.00–3.80 (several m, 4H), 3.89 (m, 9H), 4.44 (m, 1H), 4.81 (brt, 1H), 7.19 (m, 7H).

Mass Spec. (ESI): 471.4 (MH)⁺.

Example 10

N-(3,4,5-Trimethoxyphenyl)oxalyl-L-pyrrolidinylmethyl-[N',N'-4-(3-pyridyl)butyl-4-phenylbutylamino]carbamate

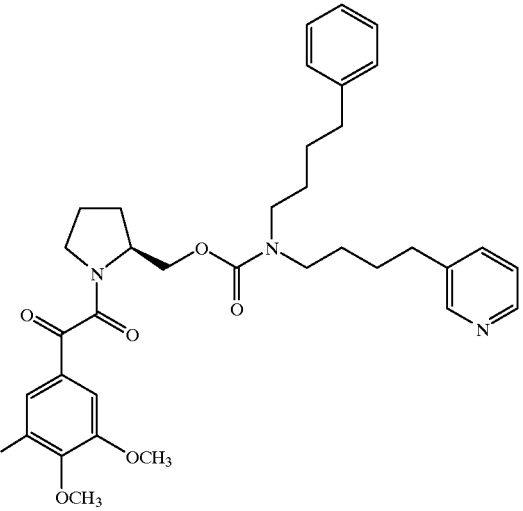

¹H-NMR δ (CDCl₃) 1.58 (8H, m), 1.95 (4H, m), 2.57 (4H, m), 2.90–3.70 (6H, 5×m), 3.90 (9H, m), 4.32 (2H, ABm), 4.50 (1H, m), 7.17 (6H, m), 7.23 (2H, s), 7.42 (2H, d), 8.42 (2H, brs).

Mass Spec. (ESI): 632.4 (MH)⁺.

Example 11

N-(3,4,5-Trimethoxyphenyl)oxalyl-L-pyrrolidinylmethyl-[N',N'-3-(3-pyridyl)propyl-4-phenylbutylamino]carbamate

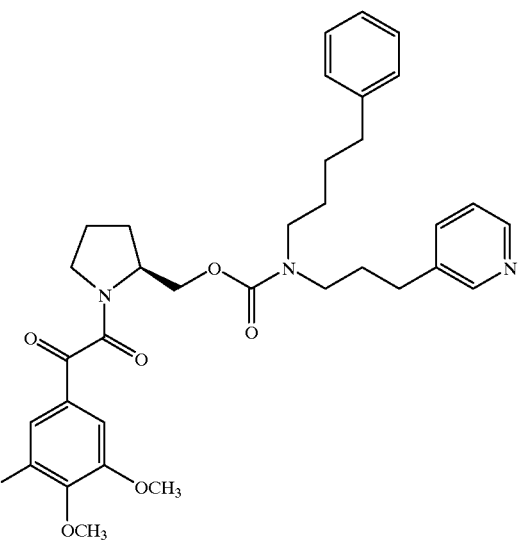

¹H-NMR δ (CDCl₃) 8.42 (d, 0.5 H); 8.39 (m, 0.5 H); 7.49–7.03 (m, 10 H); 4.49 (m, 3 H); 4.41–4.00 (m, 3 H); 3.90 (m, 9 H); 3.81–3.70 (m, 1 H); 3.63–3.02 (br m, 6 H); 2.57 (m, 2 H); 2.10–1.72 (m, 8 H).

Mass Spec. (ESI): 618.3 (MH)⁺.

Example 12

N-(3,4,5-Trimethoxyphenyl)oxalyl-L-pyrrolidinylmethyl-[N',N'-3-(3-pyridyl)propyl-2-phenylethylamino]carbamate

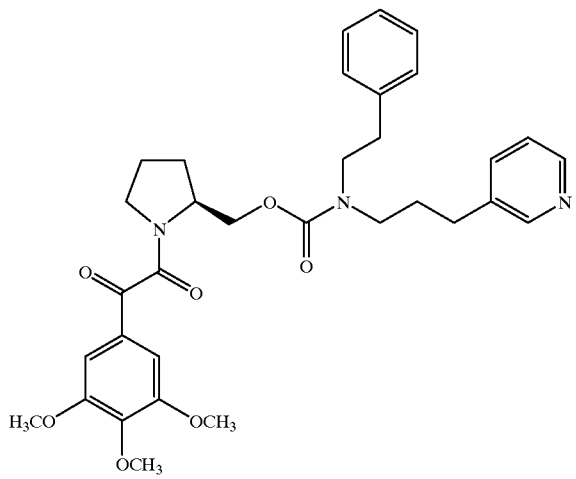

$^1$H-NMR δ (CDCl$_3$) 8.42 (d, 0.5 H); 7.43 (m, 1 H); 7.35–7.02 (br m, 9 H); 4.59–4.20 (br m, 3 H); 3.92 (m, 9 H); 3.63 (m, 1 H); 3.41 (m, 2 H); 3.21 (m, 2 H); 3.01 (m, 0.5 H); 2.81 (m, 2 H); 2.5 (t, 0.5 H); 2.57 (m, 2 H); 2.15–1.45 (m, 6H).

Mass Spec. (ESI): 590.3 (MH)$^+$.

Example 13

N-(3,4,5-Trimethoxyphenyl)oxalyl-L-pyrrolidinylmethyl-[N',N'-3-(3-pyridyl)propyl-benzylamino]carbamate

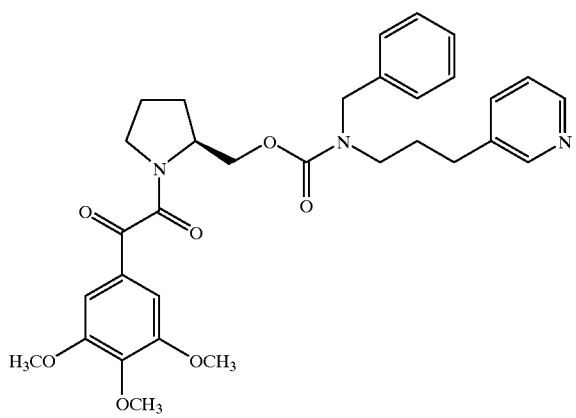

$^1$H-NMR δ (CDCl$_3$) 8.43 (m, 1 H); 7.43 (t, 1 H); 7.31–7.10 (m, 10 H); 4.55 (m, 0.5 H); 4.41 (m, 0.5 H); 4.24 (m, 1 H); 3.91 (m, 9 H); 3.51–2.98 (br m, 4 H); 2.59 (br s, 4 H); 2.05–1.71 (br m, 4 H); 1.55 (m, 2 H).

Mass Spec. (ESI): 576.3 (MH)$^+$.

Example 14

N-(3,4,5-Trimetboxyphenyl)oxalyl-L-pyrrolidinylmethyl-[N',N'-4-(3-pyridyl)butyl-3-phenylpropylamino]carbamate

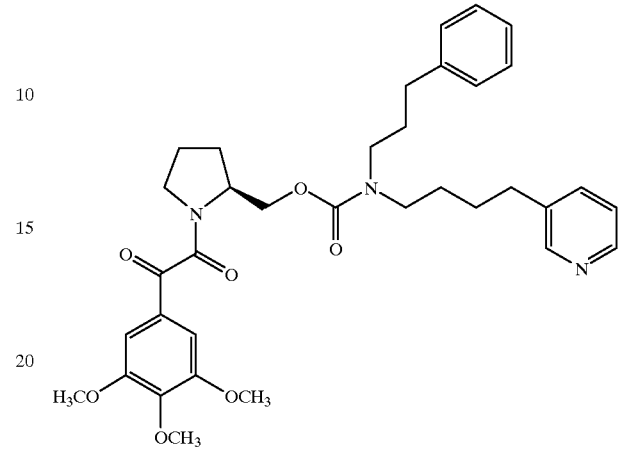

$^1$H-NMR δ (CDCl$_3$) 8.45 (m, 1.5 H); 7.51 (m, 0.5 H); 7.29–7.14 (m, 9 H); 4.59–4.21 (m, 3 H); 3.96 (s, 3 H); 3.90 (s, 3 H); 3.87 (s, 3 H); 3.43–2.95 (m, 6 H); 2.58 (m, 4 H); 2.05–1.67 (m, 6 H); 1.27 (br s, 4 H).

Mass Spec. (ESI): 618.4 (MH)$^+$.

Example 15

N-(3,4,5-Trimethoxyphenyl)oxalyl-L-pyrrolidinylmethyl-[N',N'-4-(3-pyridyl)butyl-2-phenylethylamino]carbamate

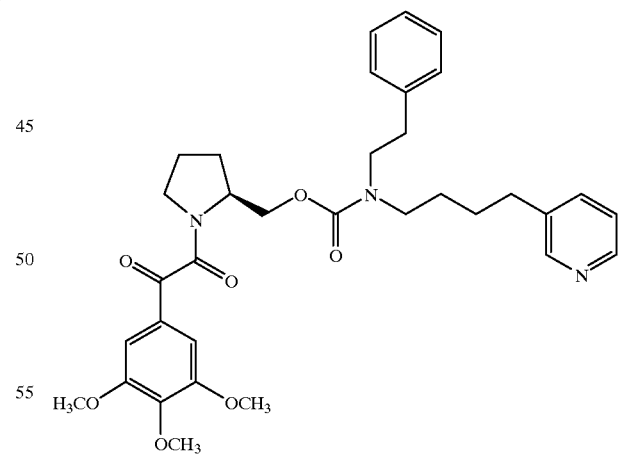

$^1$H-NMR δ (CDCl$_3$) 8.41 (s, 1 H); 7.43 (m, 1 H); 7.21 (m, 5 H); 7.19 (m, 4 H); 4.52 (m, 1 H); 4.40 (m, 1 H); 4.23 (m, 1 H); 3.93 (s, 3 H); 3.91 (s, 6 H); 3.41 (m, 4 H); 3.20 (m, 2 H); 2.81 (q, 2 h); 2.62 (m, 2 H); 1.98 (m, 4 H); 1.57 (m, 4 H).

Mass Spec. (ESI): 604.3 (MH)$^+$.

Example 16

N-(3,4,5-Trimethoxyphenyl)oxalyl-L-pyrrolidinylmethyl-[N',N'-4-(³-pyridyl)butyl-benzylamino]carbamate

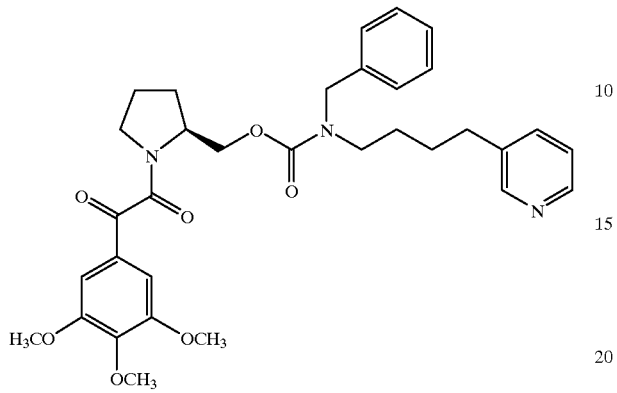

¹H-NMR δ (CDCl₃) 8.41 (m, 1.5 H); 7.43 (m, 0.5 H); 7.30–7.05 (m, 9 H); 4.46 m, 2 H); 4.37 (m, 1 H); 3.94 (s, 3 H); 3.90 (s, 6 H); 3.87 (s, 2 H); 3.47–3.11 m, 4 H); 2.59 (m, 2 H); 2.101.43 (m, 8 H).

Mass Spec. (ESI): 590.3 (MH)⁺.

Example 17

N-(3,4,5-Trimethoxyphenyl)oxalyl-L-pyrrolidinylmethyl-[N',N'-3-(3-pyridyl)propyl-3-(3-methoxyphenyl)propylamino]carbamate

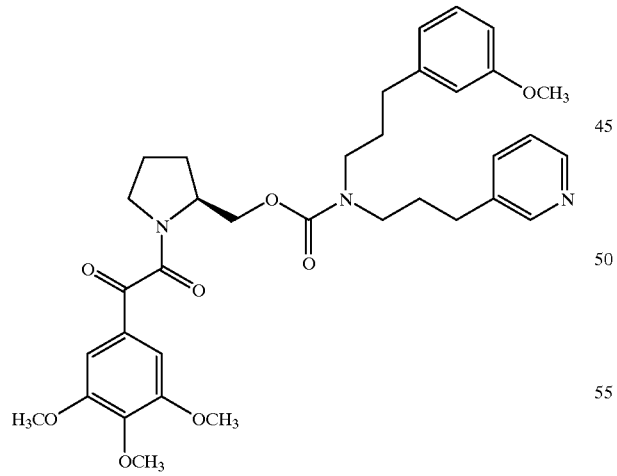

¹H-NMR δ (CDCl₃) 1.90 (m, 8H), 2.53 (m, 4H), 3.22 (m, 4H), 3.40 (m, 2H), 3.85 (m, 12H), 4.34 (m, 2H), 4.52 (m, 1H), 6.80 (m, 2H), 7.19 (t, 1H), 7.20 (ABq, 1H), 7.26 (m, 2H), 7.48 (t, 1H), 8.40 (m, 2H).

Mass Spec. (ESI): 634.43 (MH)⁺.

Example 18

N-(3,4,5-Trimethoxyphenyl)oxalyl-L-pyrrolidinylmethyl-[N',N'-3-(3-pyridyl)propyl-3-(3,4,5-trimethoxyphenyl)propylamino]carbamate

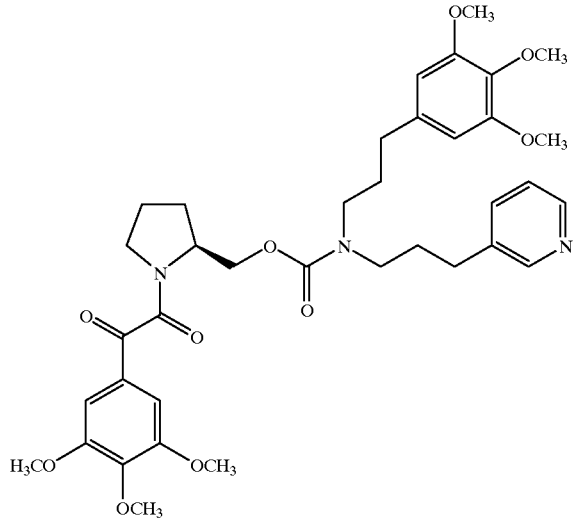

¹H-NMR δ (CDCl₃) 1.89 (m, 6H), 2.00 (m, 2H), 2.56 (2×t, 4H), 3.24 (m, 4H), 3.41 (m, 2H), 3.87 (m, 18H), 4.30 (m, 2H), 4.53 (m, 1H), 6.39 (s, 2H), 7.21 (m, 3H), 7.46 (m, 1H), 8.41 (brs, 2H).

Mass Spec. (ESI): 694.45 (MH)⁺.

Example 19

N-(3,4,5-Trimethoxyphenyl)oxalyl-(±)-piperidinylmethyl-[N',N'-3-(3-pyridyl)-propyl-3-phenyl propylamino]carbamate

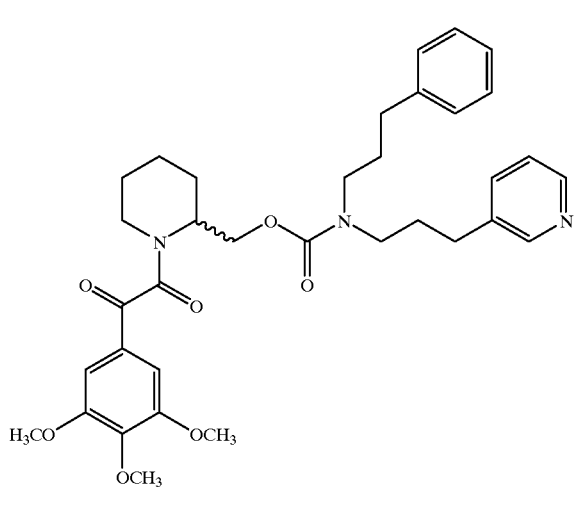

¹H-NMR δ (CDCl₃) 1.72 (m, 10H), 2.59 (m, 4H), 3.22 (m, 6H), 3.85 (s, 3H), 3.89 (s, 3H), 3.92 (s, 3H), 4.00–4.50 (m, 2H), 5.07 (m, 1H), 7.08 (s, 2H), 7.12 (m, 6H), 7.46 (d, 1H), 8.42 (brs, 2H).

Mass Spec. (ESI): 618.6 (MH)⁺.

Example 20

N,N-(3-Phenylpropyl)-3-(3-pyridyl)propyl-2-[(S)-N'-(3,4,5-trimethoxyphenyl)oxalyl-2-piperidinyl]propionamide

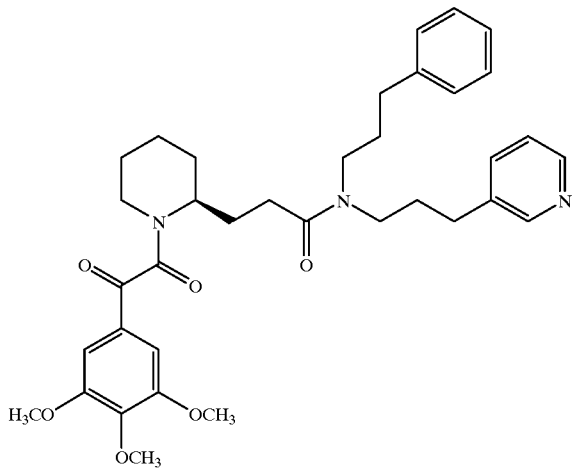

$^1$H-NMR δ (CDCl$_3$) 1.70 (m, 5 H), 1.86 (m, 6 H), 2.27 (m, 3 H), 2.61 (m, 4 H), 3.27 (m, 5 H), 3.85 (s, 3 H), 3.89 (s, 3 H), 3.93 (s, 3 H), 4.58 (m, 1 H), 4.82 (m, 1 H), 7.23 (m, 8 H), 7.52 (m, 1 H), 8.46 (m, 2 H).

Mass Spec. (ESI): 616 (MH)$^+$.

Example 21

N,N-(3-Phenylpropyl)-3-(3-pyridyl)propyl-2-[(S)-N'-(3,4,5-trimethoxyphenyl)oxalyl-2-pyrrolidinyl]propionamide

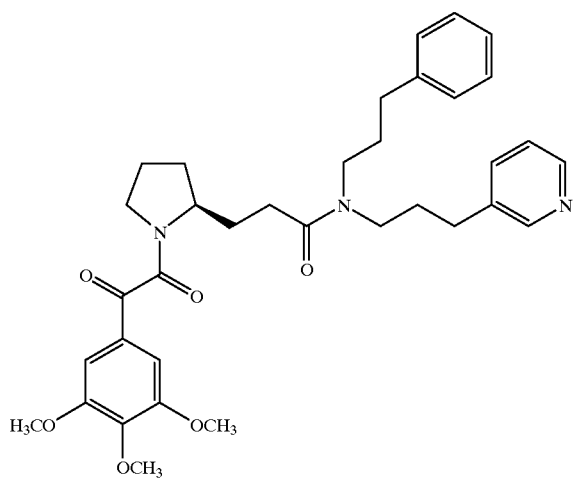

$^1$H-NMR δ (CDCl$_3$) 1.85 (m, 11H), 2.38 (dt, 1 H, J=12.8, 7.7), 2.60 (m, 4 H), 3.30 (m, 6 H), 3.95 (m, 9 H), 4.30 (m, 1 H), 7.22 (m, 8 H), 7.49 (m, 1 H), 8.44 (m, 2 H).

Mass Spec. (ESI): 602 (MH)$^+$.

Example 22

N-(3,4,5-Trimethoxyphenyl)-difluoroacetyl-L-pyrrolidinylmethyl-[N',N'-4-(3-pyridyl)butyl-4-phenylbutylamino]carbamate

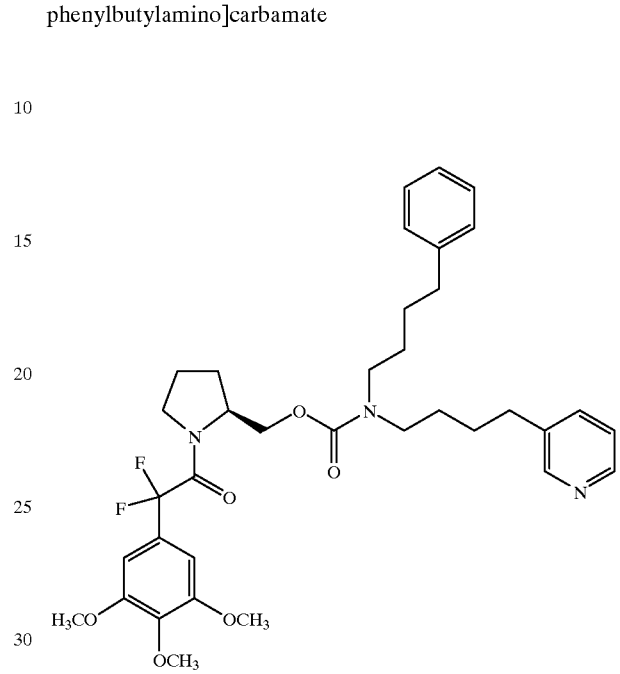

A solution of N-t-butyloxycarbonyl-L-pyrrolidinylmethyl-[N',N'-4-(3-pyridyl) butyl-4-phenylbutylamino]carbamate (50.7 mg, 0.0995 mmoles) in methylene chloride (1 mL) at rt was treated with 4M HCl in dioxane (0.25 mL, 10 equiv.). After 1 h the solvents were removed on the rotary evaporator at 30° C., and the residue flushed with dry methylene chloride (3×5 mL). The residue was dried in vacuo for 2 h, dissolved in dry methylene chloride, and then treated with 2,2-difluoro-3,4,5-trimethoxyphenylacetyl chloride (2 equiv.) and diisopropylethylamine (0.069 mL, 4 equiv.). After 12 h the mixture was concentrated in vacuo and the residue partitioned between ethyl acetate and 1M sodium hydroxide. The organic phase was washed with 1M sodium hydroxide, water and brine, dried over sodium sulfate, and evaporated. The residue was chromatographed on silica, eluting with ethyl acetate, to give the product as a colorless gum (62.5 mg, 96%).

$^1$H-NMR δ (CDCl$_3$) 1.55 (8H, m), 1.82 (4H, m), 2.60 (4H, m), 3.18 (4H, m), 3.43 (2H, m), 3.86 (9H, s), 4.22 (2H, m), 4.47 (1H, m), 6.79 (2H, s), 7.21 (6H, m), 7.48 (2H, d), 8.42 (2H, brs).

Mass Spec. (ESI): 654.4 (MH)$^+$.

The following compounds were prepared essentially as described for the previous example 22:

Example 23

N-(3,4,5-Trimethoxyphenyl)-difluoroacetyl-L-pyrrolidinylmethyl-[N',N'-3-(3-pyridyl)propyl-3-phenylpropylamino]carbamate

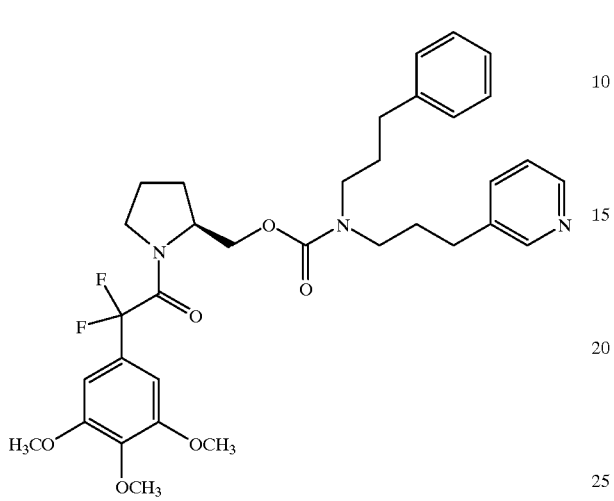

$^1$H-NMR δ (CDCl$_3$) 1.75 (m, 8H), 2.50 (m, 4H), 3.14 (m, 4H), 3.35 (m, 2H), 4.14 (m, 2H), 4.36 (m, 1H), 6.70 (s, 2H), 7.17 (m, 6H), 7.41 (m, 1H), 8.36 (m, 2H).

Mass Spec. (ESI): 626 (MH)$^+$.

Example 24

N-(3,4,5-Trimethoxyphenyl)-difluoroacetyl-L-pyrrolidinylmethyl-[N',N'-dibenzylamino]carbamate

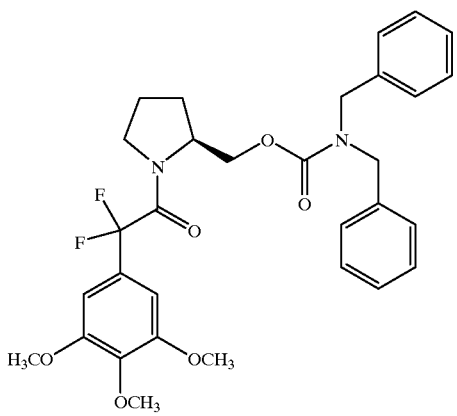

$^1$H-NMR δ (CDCl$_3$) 7.38–7.09 (m, 10 H), 6.77 (s, 2 H), 4.50–4.28 (m, 7 H), 3.85 (m, 9 H), 3.47 (m, 1 H), 3.25 (m, 1 H), 1.92–1.60 (m, 4 H).

Mass Spec. (ESI): 569.3 (MH)$^+$.

Example 25

N-(3,4,5-Trimethoxyphenyl)-difluoroacetyl-L-pyrrolidinylmethyi-[N',N'-2-(3-indolyl)ethyl-2-phenylethylamino]carbamate

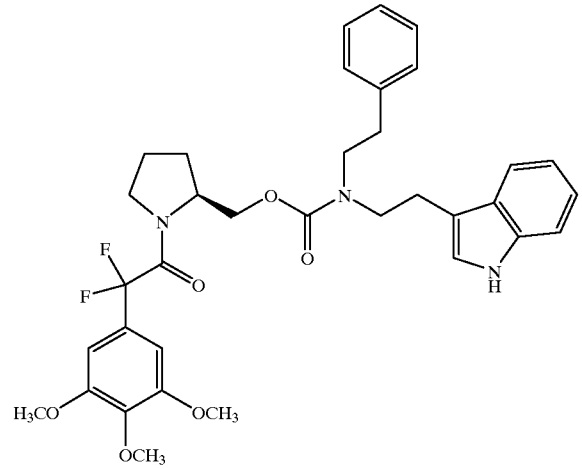

$^1$H-NMR δ (CDCl$_3$) 8.03 (bs, 1 H), 7.66–6.82 (m, 9 H), 6.79 (s, 2 H), 4.50–4.20 (m, 3 H), 3.87 (m, 9 H), 3.58–3.24 (m, 6 H), 2.98 (m, 1 H), 2.91 (m, 1 H), 2.82 (m, 1 H), 2.70 (m, 1 H), 1.97–1.70 (m, 4 H).

Mass Spec. (ESI): 636.4 (MH)$^+$.

Example 26

N-(3,4,5-Trimethoxyphenyl)-difluoroacetyl-L-pyrrolidinylmethyl-[N',N'-3-(3-pyridyl)propyl-4-phenylbutylamino]carbamate

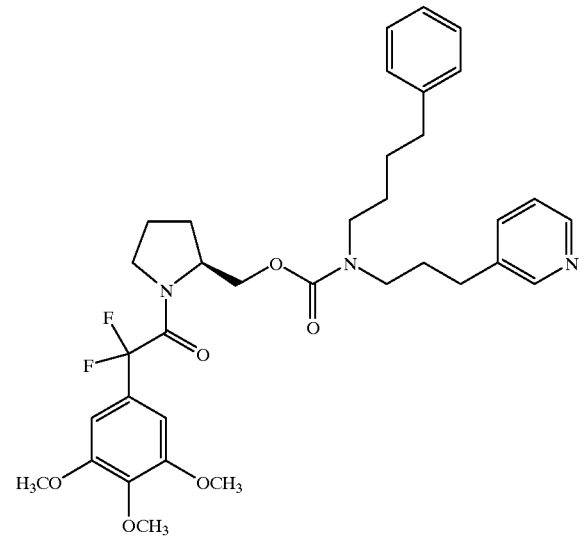

$^1$H-NMR δ (CDCl$_3$) 8.42 (m, 1 H); 7.43 (t, 1 H); 7.33–7.11 (m, 7 H); 6.79 (s, 2 H); 4.41 (m, 1 H); 4.23 (m, 3 H); 3.85 (s, 9 H); 3.55–3.38 (m, 2 H); 3.34–3.07 (m, 3 H); 2.59 (m, 4 H); 1.97–1.63 (m, 6 H), 1.55 (m, 4 H).

Mass Spec. (ESI): 640.3 (MH)$^+$.

Example 27

N-(3,4,5-Trimethoxyphenyl)-difluoroacetyl-L-pyrrolidinylmethyl-[N',N'-3-(3-pyridyl)propyl-2-phenylethylamino]carbamate

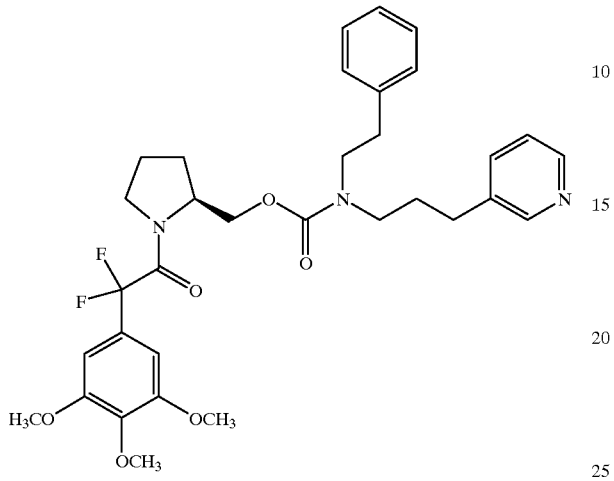

¹H-NMR δ (CDCl₃) 8.41 (m, 1 H); 7.47 (m, 1 H); 7.34–7.03 (m, 7 H); 6.73 (s, 2 H); 4.42 (m, 1 H); 4.23 (m, 2 H); 3.87 (s, 9 H); 3.57–3.04 (br m, 3 H); 2.79 (m, 2 H); 2.55 (m, 2 H) 2.00–1.69 (m, 9 H).

Mass Spec (ESI): 612.3 (MH)⁺.

Example 28

N-(3,4,5-Trimethoxyphenyl)-difluoroacetyl-L-pyrrolidinylmethyl-[N',N'-3-(3-pyridyl)propyl-benzylamino]carbamate

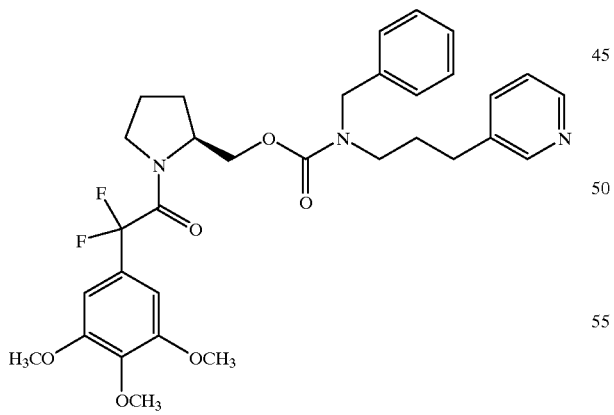

¹H-NMR δ (CDCl₃) 8.41 (d, 0.5 H); 8.39 (m, 0.5 H); 7.45–7.07 (br m, 8 H); 6.78 (s, 2 H); 4.56–4.21 (m, 4 H); 4.20–3.98 (br m, 1 H); 3.87 (s, 9 H); 3.58–3.12 (br m, 4 H); 2.59 (m, 2 H); 1.99–1.58 (br m, 6 H).

Mass Spec. (ESI): 598.3 (MH)⁺.

Example 29

N-(3,4,5-Trimethoxyphenyl)-difluoroacetyl-L-pyrrolidinylmethyl-[N',N'-4-(3-pyridyl)butyl-3-phenylpropylamino]carbamate

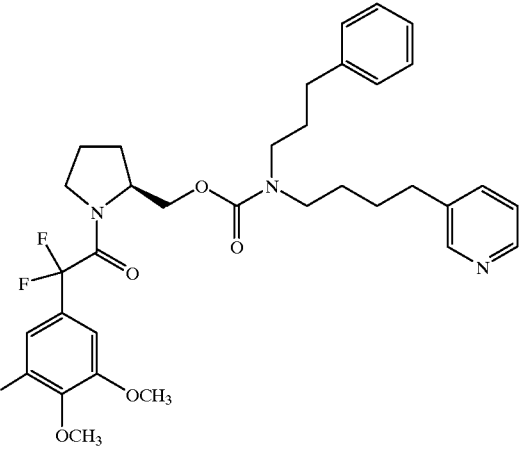

¹H-NMR δ (CDCl₃) 8.45 (m 1.5 H); 7.53 (m, 0.5 H); 7.28–7.16 (m, 7 H); 6.78 (s, 2 H); 4.23 (m, 1 H); 4.21 (m, 2 H); 3.87 (s, 9 H); 3.51–3.37 (m, 2 H); 3.25–3.05 (m, 4 H); 2.61 (m, 4 H); 1.96–1.72 (m, 6 H); 1.56 (m, 4 H).

Mass Spec. (ESI): 640.3 (MH)⁺.

Example 30

N-(3,4,5-Trimethoxyphenyl)-difluoroacetyl-L-pyrrolidinylmethyl-[N',N'-4-(3-pyridyl)butyl-2-phenylethylamino]carbamate

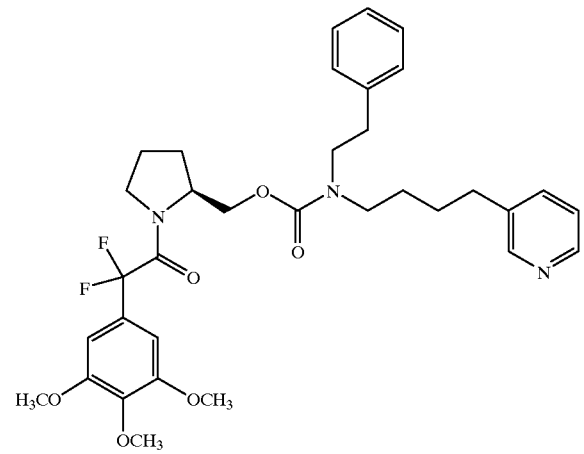

¹H-NMR δ (CDCl₃) 8.41 (s, 1 H); 7.43 (m, 1 H); 7.20 (m, 7 H); 6.79 (s, 2 H); 4.42 (m, 1 H); 4.22 (m, 2 H); 3.87 (s, 9 H); 3.41 (m, 4 H); 3.18 (m, 2 h); 2.79 (m, 2 H); 2.60 (m, 2 H); 1.82 (m, 4 H); 1.57 (m, 4 H).

Mass Spec. (ESI): 626.3 (MH)⁺; 606.3 (M-F)⁺.

Example 31

N-(3,4,5-Trimethoxyphenyl)-difluoroacetyl-L-pyrrolidinylmethyl-[N',N'-4-(3-pyridyl)butyl-benzylamino]carbamate

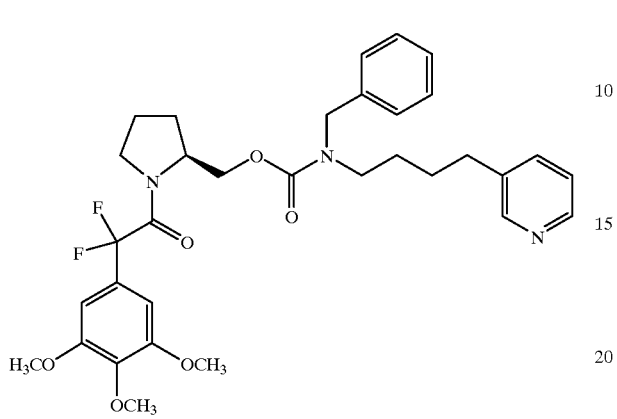

¹H-NMR δ (CDCl₃) 8.41 (m, 1.5 H); 7.43 (m, 0.5 H); 7.40–7.13 (m, 7 H); 6.79 (s, 2 H); 4.78–4.21 (m, 3 H); 3.89 (s, 9 H), 3.86 (s, 2 H); 3.58–3.09 (m, 4 H), 2.59 (m, 2 H), 1.99–1.41 (m, 8 H).

Mass Spec. (ESI): 612.4 (MH)⁺.

Example 32

N-(3,4,5-Trimethoxyphenyl)-difluoroacetyl-L-pyrrolidinylmethyl-[N',N'-3-(3-pyridyl)propyl-2-(3-methoxyphenyl)ethylamino]carbamate

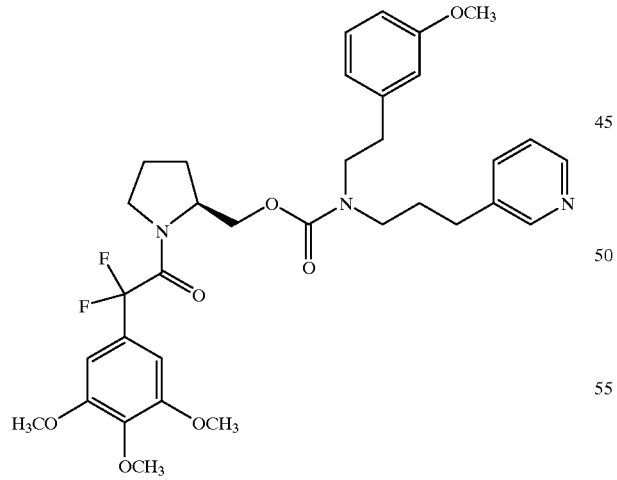

¹H-NMR δ (CDCl₃) 8.75 (m, 1 H), 8.63 (m, 1 H), 8.19 (m, 1 H), 7.80–7.28 (m, 5 H), 6.75 (s, 2 H), 4.50 (m, 1 H), 4.30–4.08 (m, 2 H), 3.86 (m, 12 H), 3.59–3.36 (m, 4 H), 3.32–3.10 (m, 2 H), 3.01–2.67 (m, 4 H), 2.02–1.69 (m, 6 H).

Mass Spec. (ESI): 642.4 (MH)⁺.

Example 33

N-(3,4,5-Trimethoxypheny))-difluoroacety-L-pyrrolidinylmethyl-[N',N'-3-(3-pyridyl)propyl-2-(3,4-dimethoxyphenyl)ethylamino]carbamate

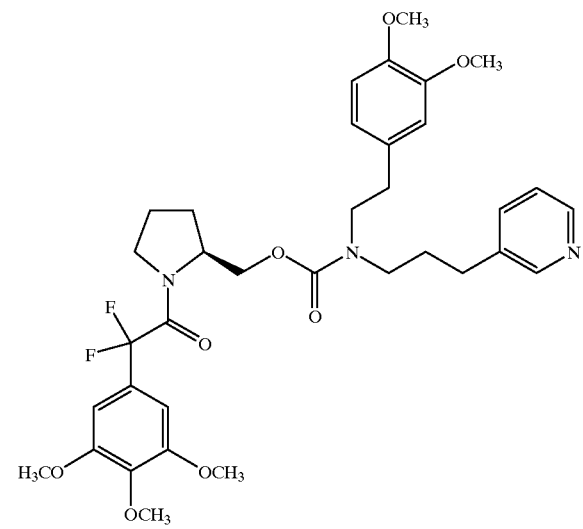

¹H-NMR δ (CDCl₃) 8.77 (m, 1 H), 8.68 (m, 1 H), 8.27–7.40 (m, 3 H), 6.82–6.63 (m, 5 H), 4.50 (m, 1 H), 4.28–4.13 (m, 2 H), 3.87 (m, 15 H), 3.54–3.31 (m, 4 H), 3.21 (m, 2 H), 2.84–2.68 (m 4 H), 2.00–1.70 (m, 6 H).

Mass Spec. (ESI): 672.4 (MH)⁺.

Example 34

N-(3,4,5-Trimethoxyphenyl)-difluoroacetyl-L-pyrrolidinylmethyl-[N',N'-3-(3-pyridyl)propyl-2-(3-trifluoromethylphenyl)ethylamino]carbamate

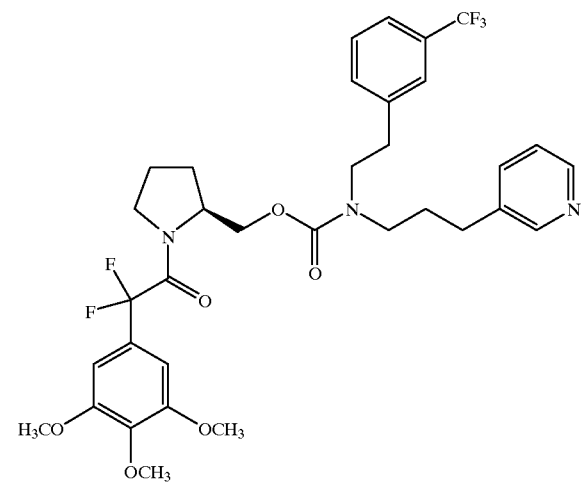

¹H-NMR δ (CDCl₃) 8.75 (m, 1 H), 8.68 (M, 1 H), 8.25–7.16 (m, 3 H), 6.82–6.65 (m, 5 H), 4.50 (m, 1 H), 4.30–4.13 (m, 2 H), 3.86 (m, 9 H), 3.55–3.33 (m, 4 H), 3.03 (m, 2 H), 2.88–2.66 (m, 4 H), 2.00–1.70 (m, 6 H).

Mass Spec. (ESI): 680.4 (MH)⁺.

Example 35

N-(3,4,5-Trimethoxyphenyl)-difluoroacetyl-L-pyrrolidinylmethyl-[N',N'-3-(3-pyridyl)propyl-3-(4-carboxyphenyl)propylamino]carbamate

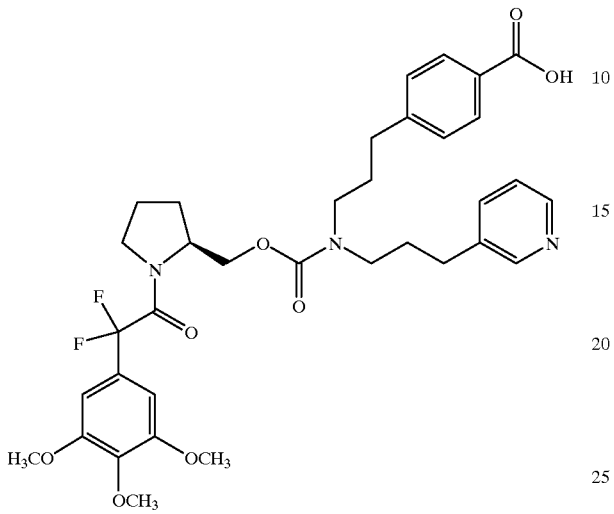

¹H-NMR δ (CDCl₃) 8.53–8.46 (m, 2 H), 8.02 (s, 1 H), 7.98 (s, 1 H), 7.72–7.19 (m, 4 H), 6.77 (s, 2 H), 4.47 (m, 1 H), 4.28–4.16 (m, 2 H), 3.86 (m, 9 H), 3.77–2.54 (m, 10 H), 1.98–1.72 (m, 8 H).

Mass Spec. (ESI): 670.4 (MH)⁺.

Example 36

N-(3,4,5-Trimethoxyphenyl)-difluoroacetyl-L-pyrrolidinylmethyl-[N',N'-3-(3-pyridyl)propyl-3-(4-benzyloxycarbonylphenyl)propylamino]carbamate

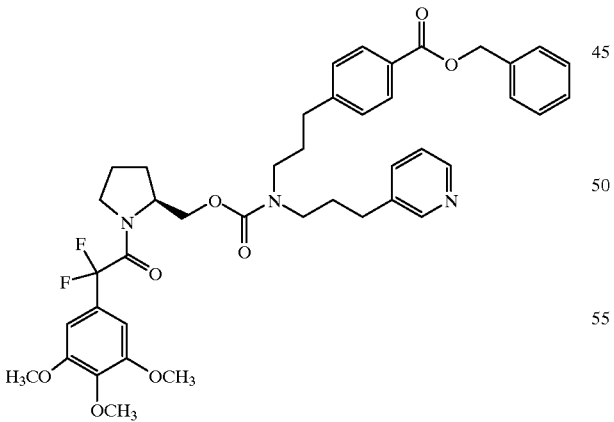

¹H-NMR δ (CDCl₃) 8.44 (m, 2 H), 8.00 (s, 1 H), 7.97 (s, 1 H), 7.61–7.18 (m, 9 H), 6.78 (s, 2 H), 5.36 (s, 2 H), 4.45 (m, 1 H), 4.26–4.14 (m, 2 H), 3.87 (m, 9 H), 3.53–3.10 (m, 6 H), 2.70–2.51 (m, 4 H), 2.00–1.70 (m, 8 H).

Mass Spec. (ESI): 670.4 (MH)⁺.

Example 37

N-(3,4,5-Trimethoxyphenyl)-difluoroacetyl-L-pyrrolidinylmethyl-[N',N'-3-(3-pyridyl)propyl-3-(3-methoxyphenyl)propylamino]carbamate

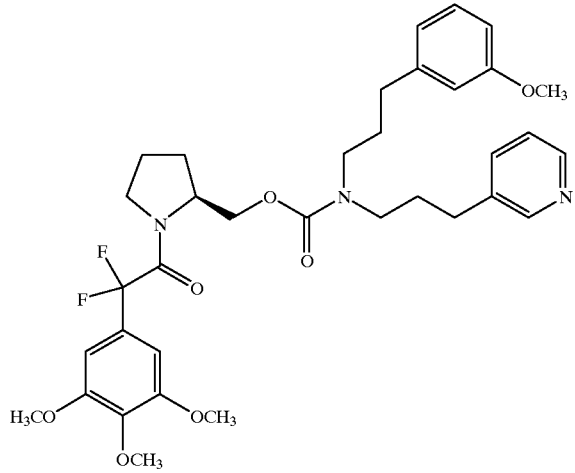

¹H-NMR δ (CDCl₃) 1.81 (m, 8H), 2.55 (m, 4H), 3.21 (m, 4H), 3.43 (m, 2H), 3.78 (s, 3H), 3.85 (m, 9H), 4.21 (m, 2H), 4.42 (m, 1H), 6.73 (m, 3H), 6.77 (s, 2H), 7.20 (m, 2H), 7.47 (brt, 1H), 8.41 (brs, 2H).

Mass Spec. (ESI): 656.41 (MH)⁺.

Example 38

N-(3,4,5-Trimethoxyphenyl)-difluoroacetyl-L-pyrrolidinylmethyl-[N',N'-3-(3-pyridyl)propyl-3-(4-methoxyphenyl)propylamino]carbamate

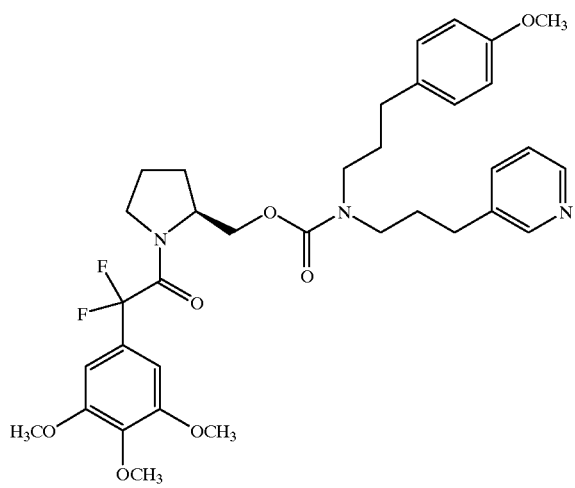

¹H-NMR δ (CDCl₃) 1.81 (m, 8H), 2.58 (m, 4H), 3.20 (m, 4H), 3.42 (m, 2H), 3.78 (s, 3H), 3.87 (m, 9H), 4.22 (ABq, 2H), 4.42 (m, 1H), 6.78 (s, 2H), 6.82 (d, 2H), 7.07 (m, 2H), 7.23 (ABq, 1H), 7.54 (m, 1H), 8.42 (brs, 2H).

Mass Spec. (ESI): 656.40 (MH)⁺.

Example 39
N-(3,4,5-Trimethoxyphenyl)-difluoroacetyl-L-pyrrolidinylmethyl-[N',N'-3-(3-pyridyl)propyl-3-(3,4,5-trimethoxyphenyl)propylamino]carbamate

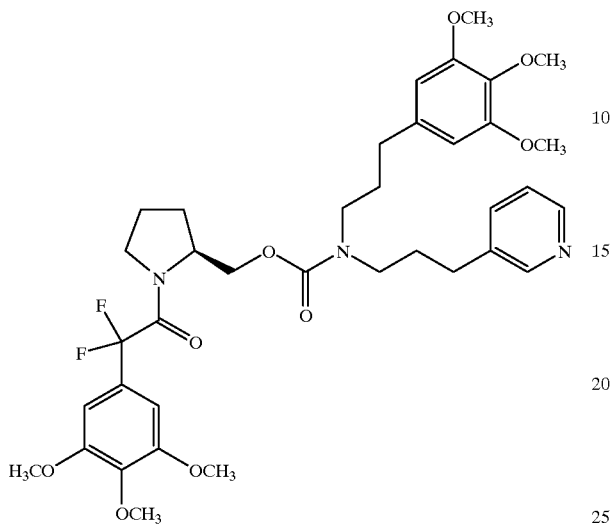

$^1$H-NMR δ (CDCl$_3$) 1.82 (m, 8H), 2.58 (m, 4H), 3.21 (m, 4H), 3.43 (m, 2H), 3.84 (m, 18H), 4.20 (ABq, 2H), 4.42 (m, 1H), 6.37 (d, 2H), 6.77 (s, 2H), 7.21 (ABq, 1H), 7.48 (brt, 1H), 8.43 (m, 2H).
Mass Spec. (ESI): 716.47 (MH)$^+$.

Example 40
N-(3,4,5-Trimethoxyphenyl)-difluoroacetyl-L-pyrrolidinylmethyl-[N',N'-3-(3-pyridyl)propyl-4-(3,4-dimethoxyphenyl)butylamino]carbamate

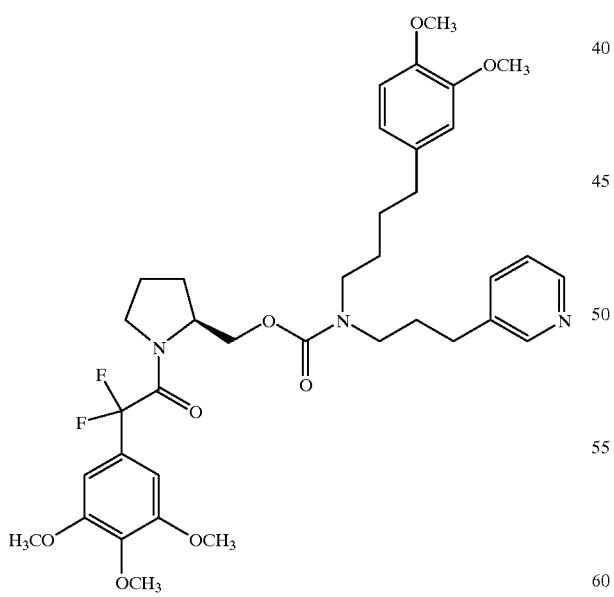

$^1$H-NMR δ (CDCl$_3$) 1.56 (m, 4H), 1.81 (m, 6H), 2.56 (m, 4H), 3.20 (m, 4H), 3.42 (m, 2H), 3.87 (m, 15H), 4.20 (m, 2H), 4.41 (m, 1H), 6.69 (brs, 2H), 6.78 (s, 2H), 6.79 (m, 1H), 7.22 (ABq, 1H), 7.50 (brt, 1H), 8.45 (m, 2H).
Mass Spec. (ESI): 700.49 (MH)$^+$.

Example 41
N-(3,4,5-Trimethoxyphenyl)-difluoroacetyl-(±)-piperidinylmethyl-[N',N'-3-(3-pyridyl)propyl-benzylamino]carbamate

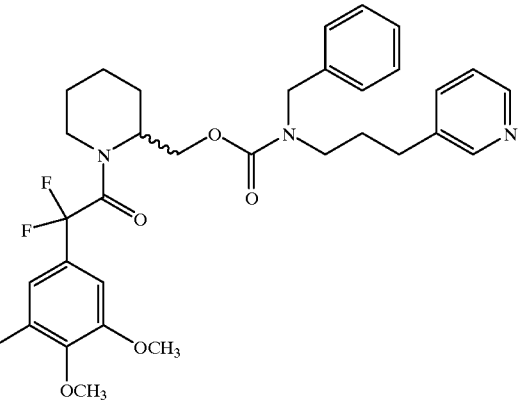

$^1$H-NMR δ (CDCl$_3$) 8.42 (d, 0.5 H); 8.40 (s, 0.5 H); 7.43 (m, 1 H); 7.21 (m, 7 h); 6.73 (d, 2 H); 5.07 (m, 1 H); 4.39 (m, 6 H); 3.85 (m, 9 H); 3.26 (t, 1 H); 3.20 (t, 1 H); 2.57 (m, 2 H); 1.84–1.35 (br m, 8 H).

Mass Spec. (ESI): 612.4 (MH)$^+$; 592.4 (M-F)$^+$.

Example 42
N-(3,4,5-Trimethoxyphenyl)-difluoroacetyl-(±)-piperidinylmethyl-[N',N'-3-(3-pyridyl)propyl-2-phenylethylamino]carbamate

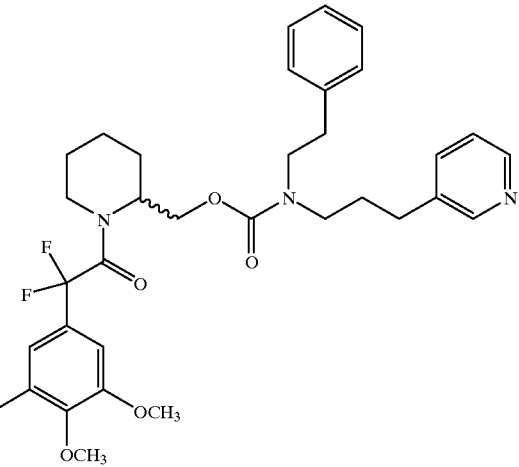

$^1$H-NMR δ (CDCl$_3$) 8.41 (s, 1 H); 7.43 (m, 1 H); 7.21 (m, 7 H); 6.73 (d, 2 H); 5.07 (m, 1 H); 4.61–4.08 (br m, 3 H); 3.87 (s, 6 H); 3.83 (s, 3 H); 3.41 (m 2 H); 3.20 (m, 3 H); 2.82 (m, 2 H); 2.59 (m, 2 H); 1.83–1.05 (br m, 8 H).

Mass Spec.: 626.4 (MH)$^+$; 606.4 (M-F)$^+$.

Example 43

N-(3,4,5-Trimethoxyphenyl)-difluoroacetyl-(±)-piperidinylmethyl-[N',N'-3-(3-pyridyl)propyl-3-phenylpropylamino]carbamate

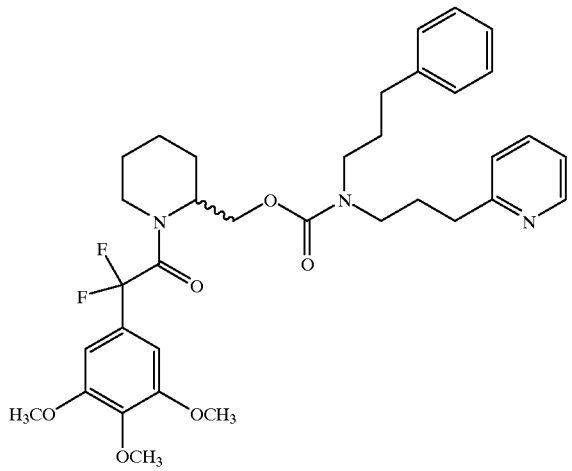

¹H-NMR δ (CDCl₃) 8.41 (s, 1 H); 7.51 (m, 1 H); 7.22 (m, 7 H); 6.73 (s, 2 H); 5.07 (m, 1 H); 4.60–4.09 (br m, 3 H); 3.87 (s, 6 H); 3.83 (s, 3 H); 3.74 (m, 1 H); 3.33–3.01 (br m, 2.5 H); 2.82 (m, 0.5 H); 2.61 (m, 2 H); 1.84–1.01 (br m, 15 H).

Mass Spec.: 654.5 (MH)⁺; 634.5 (M-F)⁺.

Example 44

N,N-(3-Phenylpropyl)-3-(3-pyridyl)propyl-2-[(S)-N'-(3,4,5-Trimethoxyphenyl)-difluoroacetyl-2-piperidinyl]propionamide

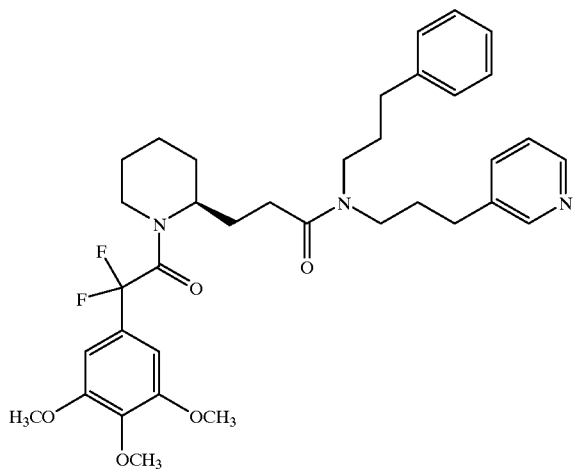

¹H-NMR δ (CDCl₃) 1.50 (m, 6 H), 1.83 (m, 5 H), 2.20 (m, 3 H), 2.60 (m, 4 H), 3.03 (m, 1 H), 3.21 (m, 2 H), 3.34 (m, 2 H), 3.68 (m, 1 H), 3.85 (s, 3 H), 3.86 (s, 3 H), 3.87 (s, 3 H), 4.76 (m, 1 H), 6.74 (m, 2 H), 7.24 (m, 6 H), 7.50 (m, 1 H), 8.44 (m, 2 H).

Mass Spec. (ESI): 638 (MH)⁺.

Example 45

N,N-(3-Phenylpropyl)-3-(3-pyridyl)propyl-2-[(S)-N'-(3,4,5-Trimethoxyphenyl)-difluoroacetyl-2-pyrrolidinyl]propionamide

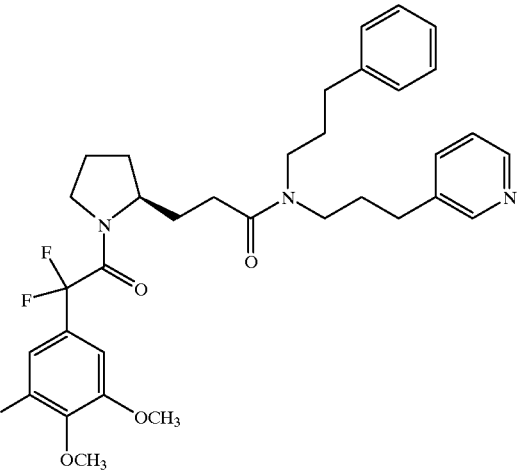

¹H-NMR δ (CDCl₃) 1.75 (m, 10 H), 2.26 (m, 2 H), 2.59 (m, 4 H), 3.24 (m, 2 H), 3.34 (m, 2 H), 3.45 (m, 2 H), 3.85 (m, 9 H), 4.19 (m, 1 H), 6.67 (m, 2 H), 7.24 (m, 6 H), 7.50 (m, 1 H), 8.43 (m, 2 H).

Mass Spec. (ESI): 624 (MH)⁺.

Example 46

FKBP12 Rotamase Inhibition Assay

The rotamase activity of FKBP-12 was measured by an adaptation of the assay described by Kofron et al. (*Biochemistry*, 30, pp. 6127–6134 (1991)). The assay was carried out at 4° C. with 1 mg chymotrypsin/mL of assay with succinyl-Ala-Leu-Pro-Phe-p-nitroanilide as the substrate. Chymotrypsin rapidly hydrolyzes the peptide bond on the C-terminal side of the Phe of the trans form of the peptide and releases the chromogenic p-nitroaniline. The rate of the reaction is controlled by the rate of conversion of the cis form of the peptide to the trans-form, the reaction catalyzed by FKBP12. The apparent $K_i$ values for inhibition of the rotamase activity were determined by measuring decreases in the first order rate constant of the reaction catalyzed by FKBP12 as a function of the concentrations of the compounds described herein. Ki is the concentration of the compound that causes 50 percent inhibition of rotamase activity which is indicative of neurite outgrowth activity. The results are presented in Tables 1-4.

Example 47

Assay of Neurite Outgrowth in PC12 Cell Cultures

PC-12A rat pheochromocytoma cells are maintained in Dulbecco's modified Eagle's medium (DMEM) supplemented with 10% fetal calf serum and 5% calf serum at 37° C. and 5% $CO_2$. Cells to be assayed are plated at $10^4$ per well of a 24 well plate and allowed to attach for 4–18 h. The medium is then replaced with DMEM plus 0.1% BSA, submaximal concentrations of nerve growth factor (NGF)

(as determined by neurite outgrowth assay), and varying concentrations of the FKBP12 binding compound (0.1 nM–10 μM) in a final concentration of 0.25% DMSO. Control cultures are treated with NGF in the absence of the FKBP12 binding compound. After 72 h, cultures are fixed with 4% formalin in PBS, stained with Commassie Blue, and approximately 200 cells are counted in random fields of each well. Cells with neurites longer than one cell diameter are counted as a percentage of total number of cells.

The FKBP12 binding compounds of formula I utilized in this invention cause a significant increase in neurite outgrowth over control cultures.

Additionally, compounds of this invention may also show benefit as reversers of multidrug resistance (MDR) in cancer chemotherapy and as agents for the treatment of HIV infection. Nonimmunosuppressive compounds possessing the structural elements of the FKBP12 binding portion of FK506 have shown utility in reversing P-glycoprotein mediated MDR (U.A. Germann, et al., *Anti-Cancer Drugs*, 8, pp. 125–140 (1997)). In addition, there has been no direct correlation shown between rotamase inhibitory activity and MDR reversing activity (J. R. Hauske, et al., *Bioorg. Med. Chem. Len.*, 4, pp. 2097–2102 (1994)). In the area of HIV infection, it is known that immunophilins, including the FK506 binding proteins (FKBPs), are involved in facilitating binding of the HIV envelope protein gp120 to host CD4 receptors (M. M. Endrich, et al., *Eur. J. Biochem.*, 252, pp. 441–446 (1998)), and that FK506 inhibits the growth of HIV-infected cells (A. Karpas, et al., *Proc. Natl. Acad. Sci USA*, 89, pp. 8351–8355 (1992)).

TABLE 2

FKBP12 rotamase inhibition data with selected examples

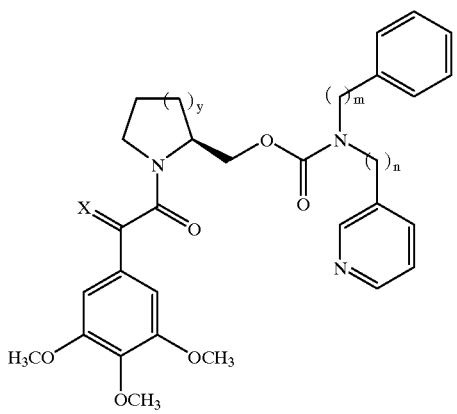

| Example # | y | X | n | m | % inhib. at 10 μM or 1 μM* | $K_i$, nM |
|---|---|---|---|---|---|---|
| 13 | 1 | O | 3 | 1 | 79 | |
| 28 | 1 | $F_2$ | 3 | 1 | 99 | 577 |
| 12 | 1 | O | 3 | 2 | 80 | |
| 27 | 1 | $F_2$ | 3 | 2 | 97 | 234 |
| 7 | 1 | O | 3 | 3 | 100 | 447 |
| 23 | 1 | $F_2$ | 3 | 3 | 98 | 113 |
| 11 | 1 | O | 3 | 4 | 96 | 537 |
| 26 | 1 | $F_2$ | 3 | 4 | 99 | 158 |
| 16 | 1 | O | 4 | 1 | 18* | |

TABLE 1

FKBP12 rotamase inhibition data with selected examples

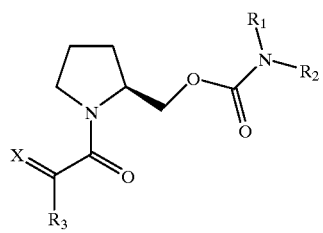

| Ex. # | $R_1$ | $R_2$ | $R_3$ | X | % inhib. at 10 μM or 1 μM* |
|---|---|---|---|---|---|
| 1 | 3-phenylpropyl | 3-(3-pyridyl)-propyl | t-butyl | O | 93 |
| 4 | H | 3-pyridylmethyl | t-butyl | O | 12 |
| 3 | benzyl | 2-phenylethyl | t-butyl | O | 39 |
| 2 | benzyl | benzyl | t-butyl | O | 27 |
| 5 | H | 2-phenylethyl | t-butyl | O | 0 |
| 8 | H | 3-pyridylmethyl | 3,4,5,-trimethoxyphenyl | O | 11 |
| 6 | H | 3-phenylpropyl | t-butyl | O | 32 |
| 9 | H | 2-phenylethyl | 3,4,5,-trimethoxyphenyl | O | 11 |
| 25 | 2-phenylethyl | indolylethyl | 3,4,5-trimethoxyphenyl | $F_2$ | 11* |
| 24 | Benzyl | benzyl | 3,4,5-trimethoxyphenyl | $F_2$ | 34* |

TABLE 2-continued

FKBP12 rotamase inhibition data with selected examples

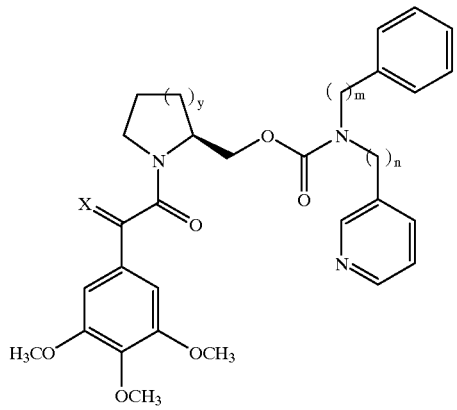

| Example # | y | X | n | m | % inhib. at 10 μM or 1 μM* | $K_i$, nM |
|---|---|---|---|---|---|---|
| 31 | 1 | $F_2$ | 4 | 1 | 63* | 686 |
| 15 | 1 | O | 4 | 2 | 82 | |
| 30 | 1 | $F_2$ | 4 | 2 | 97 | |
| 14 | 1 | O | 4 | 3 | 54* | |
| 29 | 1 | $F_2$ | 4 | 3 | 80* | |
| 10 | 1 | O | 4 | 4 | 52* | |
| 22 | 1 | $F_2$ | 4 | 4 | 83* | 271 |
| 41 | 2 | $F_2$ | 3 | 1 | 11* | |
| 42 | 2 | $F_2$ | 3 | 2 | 1* | |
| 19 | 2 | O | 3 | 3 | 11 | |
| 43 | 2 | $F_2$ | 3 | 4 | 0* | |

TABLE 3

FKBP12 rotamase inhibition data with selected examples

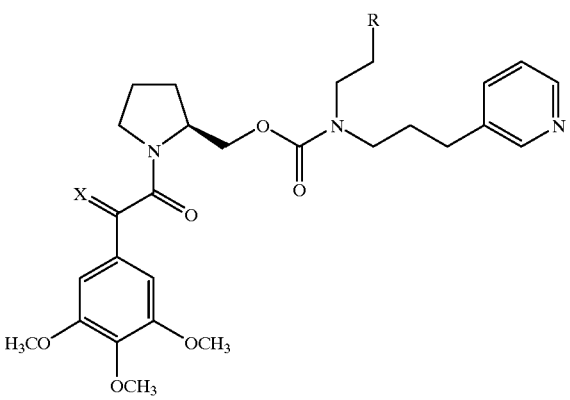

| Example # | R | X | % rotamase inhib. at 1 μM |
|---|---|---|---|
| 32 | 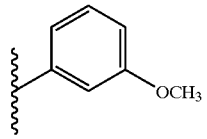 | $F_2$ | 93 |

TABLE 3-continued

FKBP12 rotamase inhibition data with selected examples

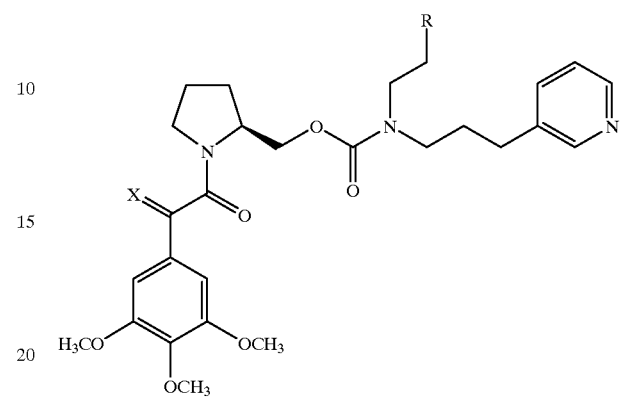

| Example # | R | X | % rotamase inhib. at 1 μM |
|---|---|---|---|
| 33 | 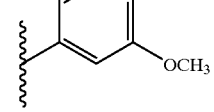 | $F_2$ | 96 |
| 34 | 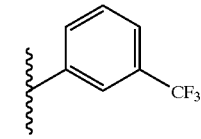 | $F_2$ | 96 |
| 37 | 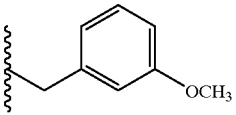 | $F_2$ | 93 |
| 17 | 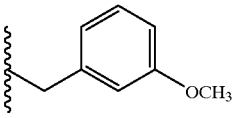 | O | 75 |
| 38 | 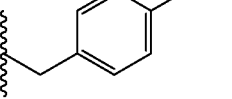 | $F_2$ | 95 |
| 39 | 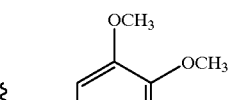 | $F_2$ | 92 |

TABLE 3-continued

FKBP12 rotamase inhibition data with selected examples

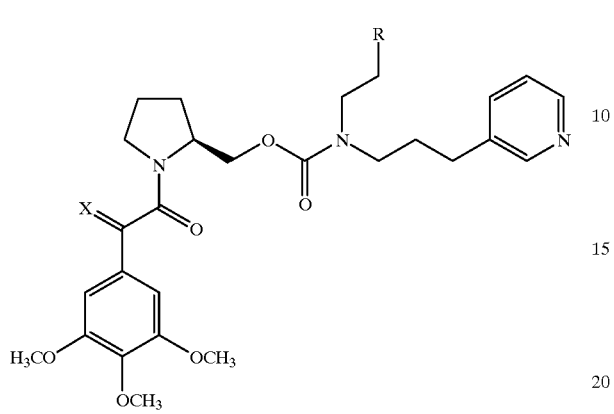

| Example # | R | X | % rotamase inhib. at 1 μM |
|---|---|---|---|
| 18 | 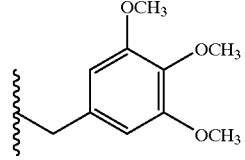 | O | 68 |
| 35 | 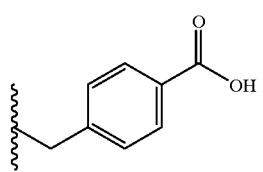 | F$_2$ | 94 |
| 36 | 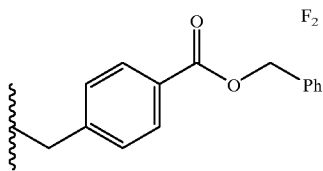 | F$_2$ | 77 |
| 40 | 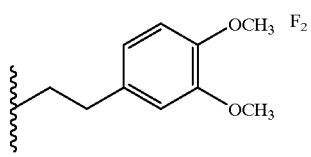 | F$_2$ | 98 |

TABLE 4

FKBP12 rotamase inhibition data with selected examples

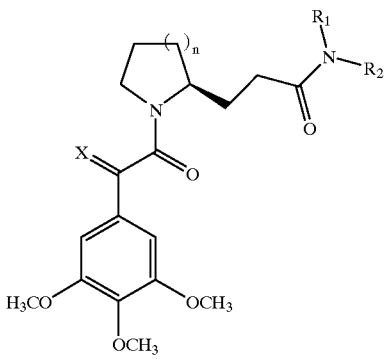

| Example # | n | R$_1$ | R$_2$ | X | % rotamase inhib. at 1 μM |
|---|---|---|---|---|---|
| 20 | 2 | 3-phenylpropyl | 3-(3-pyridyl)-propyl | O | 0 |
| 44 | 2 | 3-phenylpropyl | 3-(3-pyridyl)-propyl | F$_2$ | 0 |
| 21 | 1 | 3-phenylpropyl | 3-(3-pyridyl)-propyl | O | 1 |
| 45 | 1 | 3-phenylpropyl | 3-(3-pyridyl)-propyl | F$_2$ | 42 |

If pharmaceutically acceptable salts of the compounds of formula I are used, those salts are preferably derived from inorganic or organic acids and bases. Included among such acid salts are the following: acetate, aspartate, bisulfate, butyrate, citrate, fumarate, hydrochloride, hydrobromide, hydroiodide, lactate, maleate, oxalate, persulfate, propionate, succinate, tartrate. Base salts include ammonium salts, alkali metal salts, such as sodium and potassium salts, alkaline earth metal salts, such as calcium and magnesium salts, salts with organic bases, such as dicyclohexylamine salts, N-methyl-Dglucamine, and salts with amino acids such as arginine, lysine, and so forth.

Pharmaceutically acceptable carriers that may be used in these pharmaceutical compositions include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

The compositions of the present invention may be administered orally, parenterally, by inhalation spray, topically, rectally, nasally, buccally, vaginally or via an implanted reservoir.

It should also be understood that a specific dosage and treatment regimen for any particular patient will depend upon a variety of factors, including the activity of the specific compound employed, the age, body weight, general health, sex, diet, time of administration, rate of excretion, and the judgment of the treating physician and the severity of the particular disease being treated. The amount of compound of formula I will also depend upon the particular FKBP12 binding compound in the composition.

The amount of compound of formula I utilized in these methods is between bout 0.01 and 100 mg/kg body weight/day.

What is claimed is:
1. A compound having the formula (I)

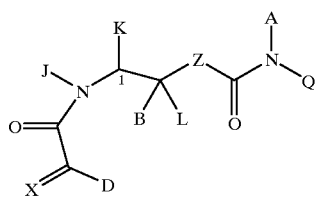

and pharmaceutically acceptable salts thereof, wherein:
Z is O, NH, or N($C_1$–$C_3$)-alkyl;
X is O or $F_2$;
B and L are independently hydrogen, ($C_1$–$C_4$)-alkyl, or benzyl;
J and K together with the atoms to which they are attached form a 5-membered ring containing one nitrogen as the only heteroatom;
wherein the stereochemistry at carbon position 1 is R or S;
D is ($C_1$–$C_6$)-straight or branched alkyl, ($C_2$–$C_6$)-straight or branched alkenyl, ($C_5$–$C_7$)-cycloalkyl or ($C_5$–$C_7$)-cycloalkenyl substituted with ($C_1$–$C_4$)-straight or branched alkyl or ($C_2$–$C_4$)-straight or branched alkenyl, O-($C_1$–$C_4$)-straight or branched alkyl, O-($C_2$–$C_4$)-straight or branched alkenyl, 2-indolyl, 3-indolyl, [($C_1$–$C_4$)-alkyl or ($C_2C_4$)-alkenyl]-Ar or Ar;
Ar is a carbocyclic aromatic group selected from the group consisiting of phenyl, 1-naphthyl, 2-naphthyl, indenyl, azulenyl, fluorenyl, and anthracenyl; or a heterocyclic aromatic group selected from the group consisting of 2-furyl, 3-furyl, 2-thienyl, 3-thienyl, 2-pyridyl, 3-pyridyl, 4pyridyl, pyrrolyl, oxazolyl, thiazolyl, imidazolyl, pyrazolyl, isoxazolyl, isothiazolyl, 1,2,3-oxadiazolyl, 1,2,3-triazolyl, 1,3,4-thiadiazolyl, pyridazinyl, pyrimidinyl, pyrazinyl, 1,3,5-triazinyl, 1,3,5-trithianyl, indolizinyl, indolyl, isoindolyl, 3H-indolyl, indolinyl, benzo[b]furanyl, benzo[b]thiophenyl, 1H-indazolyl, benzimidazolyl, benzthiazolyl, purinyl, 4H-quinolizinyl, quinolinyl, isoquinolinyl, cinnolinyl, phthalazinyl, quinazolinyl, quinoxalinyl, 1,8-naphthyridinyl, pteridinyl, carbazolyl, acridinyl, phenazinyl, phenothiazinyl, and phenoxazinyl;
Ar may contain one to three substituents which are independently selected from the group consisting of hydrogen, halogen, hydroxyl, hydroxymethyl, nitro, trifluoromethyl, trifluoromethoxy, ($C_1$–$C_6$)-straight or branched alkyl, ($C_2$–$C_6$)-straight or branched alkenyl, O-[($C_1$–$C_4$)-straight or branched alkyl], O-benzyl, O-phenyl, 1,2-methylenedioxy, amino, carboxyl, N-[($C_1$–$C_5$)-straight or branched alkyl or ($C_2$–$C_5$)-straight or branched alkenyl] carboxamides, N,N-di-[($C_1$–$C_5$)-straight or branched alkyl or ($C_2$–$C_5$)-straight or branched alkenyl] carboxamides, N-morpholinecarboxamide, N-benzylcarboxamide, N-thiomorpholinocarboxamide, N-picolinoylcarboxamide, O—W, $CH_2$—$(CH_2)_p$—W, O—$(CH_2)_p$—W, $(CH_2)_p$—O—W, and CH=CH—W;
W is 4-methoxyphenyl, 2-pyridyl, 3-pyridyl, 4-pyridyl, pyrazyl, quinolyl, 3,5-dimethylisoxazoyl, isoxazoyl, 2-methylthiazoyl, thiazoyl, 2-thienyl, 3-thienyl, or pyrimidyl; p is 0–2;

Q and A are independently hydrogen, Ar, ($C_1$–$C_{10}$)-straight or branched alkyl, ($C_2$–$C_{10}$)-straight or branched alkenyl or alkynyl, provided the carbon atom having the triple bond in the alkynyl group is not directly bonded to the nitrogen atom of the core; ($C_5$–$C_7$)-cycloalkyl substituted ($C_1$–$C_6$)-straight or branched alkyl, ($C_2$–$C_6$)-straight or branched alkenyl or alkynyl, ($C_5$–$C_7$)-cycloalkenyl substituted ($C_1$–Ce)-straight or branched alkyl, ($C_2$–$C_6$)-straight or branched alkenyl or alkynyl, or Ar-substituted ($C_1$–$C_6$)-straight or branched alkyl, ($C_2$–$C_6$)-straight or branched alkenyl or alkynyl wherein, in each case, any one of the $CH_2$ groups of said alkyl, alkenyl or alkynyl chains may be optionally replaced by a heteroatom selected from the group consisting of O, S, SO, $SO_2$, N, and NR, wherein R is selected from the group consisting of hydrogen, ($C_1$–$C_4$)-straight or branched alkyl, ($C_2$–$C_4$)-straight or branched alkenyl or alkynyl, and ($C_1$–$C_4$)-bridging alkyl wherein a bridge is formed between the nitrogen and a carbon atom of said heteroatom-containing chain to form a ring, and wherein said ring is optionally fused to an Ar group; or

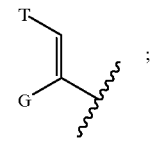

G is hydrogen, ($C_1$–$C_6$)-straight or branched alkyl or ($C_2$–$C_6$)-straight or branched alkenyl or alkynyl; and
T is Ar or substituted 5–7 membered cycloalkyl with substituents at positions 3 and 4 which are independently selected from the group consisting of oxo, hydrogen, hydroxyl, O-($C_1$–$C_4$)-alkyl, or O-($C_2$–$C_4$)-alkenyl.
2. A compound of claim 1 wherein:
J and K are taken together to form a pyrrolidine ring;
the stereochemistry at carbon 1 is S;
B and L are each hydrogen;
X is $F_2$ or O;
Z is O;
D is 3, 4, 5 trimethoxyphenyl or t-butyl;
A is 3-(3-pyridyl)propyl or 4-(3-pyridyl)butyl; and
Q is phenyl-substituted ($C_1$–$C_6$)alkyl, wherein phenyl is optionally substituted with one to three substituants independently selected from ($C_1$–$C_6$) alkyl, O-($C_1$–$C_6$) alkyl, carboxyl and trifluoromethyl, wherein said alkyl is straight or branched.
3. A compound of claim 2 wherein Q is:
3-phenylpropyl;
3-(3,4,5-trimethoxyphenyl)propyl;
2-(3,4-dimethoxyphenyl)ethyl;
2-phenylethyl;
4-phenylbutyl;
4-(3,4-dimethoxyphenyl)butyl;
3-(4-carboxyphenyl)propyl;
2-(3-methoxyphenyl)ethyl;
2-(3-trifluoromethylphenyl)ethyl, or
3-(4-methoxyphenyl)propyl.
4. A pharmaceutical composition which compises as an active ingredient an amount of a compound as claimed in claim 1, or a pharmaceutically acceptable salt thereof, effective for stimulating neurite growth in nerve cells, and one or more pharmaceutically acceptable carriers, excipients or diluents thereof.

5. A pharmaceutical composmion which comprises as an active ingredient an amount of a compound as claimed in any one of claims 2 to 3, or a pharmaceutically acceptable salt thereof, effective for stimulating neurite growth in nerve cells, and one or more pharmaceutically acceptable carriers, excipients or diluents thereof.

6. A method for stimulating neurite growth in nerve cells comprising the step of contacting said nerve cells with a neurotrophic amount of a compound with affinity for an FK-506 binding protein as claimed in any one of claims 1–3.

7. A method for stimulating neurite growth in nerve cells comprising the step of contacting said nerve cells with a neurotrophic amount of a compound with affinity for FKBP12 as claimed in any one of claims 1–3.

* * * * *